US006984619B1

(12) United States Patent
Grdina et al.

(10) Patent No.: US 6,984,619 B1
(45) Date of Patent: Jan. 10, 2006

(54) METHOD FOR PROTECTION AGAINST TUMOR METASTASIS FORMATION

(75) Inventors: David J. Grdina, Naperville, IL (US); Luka Milas, Houston, TX (US)

(73) Assignees: Arch Development Corporation, Chicago, IL (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/523,886

(22) Filed: Mar. 13, 2000

Related U.S. Application Data

(60) Provisional application No. 60/125,605, filed on Mar. 19, 1999.

(51) Int. Cl.
*A01N 61/00* (2006.01)
*C12Q 1/00* (2006.01)
*C12Q 1/68* (2006.01)

(52) U.S. Cl. .................................. 514/1; 435/4; 435/6
(58) Field of Classification Search .................... 514/1, 514/44; 435/4, 6
See application file for complete search history.

(56) References Cited

U.S. PATENT DOCUMENTS

| 5,488,042 A | 1/1996 | Grdina ........................ 514/114 |
| 5,567,686 A | 10/1996 | Grdina ........................ 514/43 |
| 5,837,696 A * | 11/1998 | Golub et al. ................. 514/153 |
| 5,869,338 A | 2/1999 | Grdina ........................ 435/375 |
| 5,891,856 A | 4/1999 | Grdina ........................ 514/43 |

FOREIGN PATENT DOCUMENTS

| WO | WO 93/17689 | 9/1993 |
| WO | WO 95/07700 | 3/1995 |

OTHER PUBLICATIONS

Hasegawa et al., Matrilysin-Specific Antisense Oligonucleotide Inhibits Liver Metastasis of Human Colon Cancer Cells in a Nude Mouse Model, 1998, Int. J. Cancer, vol. 76, pp. 812-816.*
Milas et al.; Effect of Tumor type, Size, and Endpoint on Tumor Radioprotection by WR-2721; 1984, Int. J. Radiation Oncology Biol. Phys., vol. 10: 41-48.
Gura, T., 1997, Science, vol. 278, p. 1041-1042.*
Wattenberg, L., 1997, Proceedings of the Society for Experimental Biology and Medicine, vol. 216, No. 2, p. 133-141.*
Lesniak et al., 2001, Current Neurology and Neuroscience Reports, vol. 1, p. 210-216.*
Grdina et al., "Prevention of spontaneous metastases formation in murine tumor models by Amifostine," *Proc. Americ. Ass. Canc. Res. Ann. Meet.*, No. 40, pp. 485, 2000.

Miele et al., "Enhanced metastatic ability of TNF-α-treated malignant melanoma cells is reduced by intercellular adhesion molecule-1 (ICAM-1, CD54) antisense oligonucleotides," *Expermntl. Cell Reser.*, 214:231-241, 1994.
Milas et al., "Protective effects of thiol compound WR-2721 against metastasis enhancement caused by cyclophosphamide (CY) and whole-body irradiation (WBI)," *Proc. Amer. Ass. Canc. Res.*, 25:62, 1984.
Ulrich et al., "Influence of WR-2721 on metastatic tumor spread after irradiation," *Proc. Third. Ann. Meet. SE. Canc. Res. Ass.*, 1976.
Albini et al., "Inhibition of invasion, gelatinase activity, tumor take and metastasis of malignant cells by N-acetylcysteine," *Int. J. Cancer*, 61:121-129, 1995.
Antras-Ferry, J. et al., "Oltipraz stimulates the transcription of the manganese superoxide dismutase gene in rat hepatocytes," *Carcinogenesis*, 18:2113-2117, 1997.
Apffel, C.A. et al., "Tumor rejection in experimental animals treated with radioprotective thiols," *Cancer Res.*, 35:429-437, 1975.
Banner et al., "Experimental chelation therapy in chromium, lead, and boron intoxication with N-acetylcysteine and other compounds," *Toxicol. Appl. Pharmacol.*, 83:142-147, 1986.
Brumas et al., "Can N-acetyl-L-cysteine affect zinc metabolism when used as a paracetamol antidote?" *Agents Actions*, 36:278-288, 1992.
Carnes, B.A. et al., "In vivo protection by the aminothiol WR-2721 against neutron-induced carcinogenesis," *Int. J. Radiat. Biol.*, 61:567-576, 1992.
Das, K.C. et al., "Activation of NF-kB and elevation of MnSOD gene expression by thiol reducing agents in lung adenocarcinoma (A549) cells," *Am J. Physiol.*, 269:L588-L602, 1995.
De Flora et al., "Chemopreventive properties and mechanisms of N-acetylcysteine. The experimental background," *J. Cell Biochem. Suppl.*, 22:33-41, 1995.
De Flora et al., "Synergism between N-acetylcysteine and doxorubicin in the prevention of tumorigenicity and metastasis in murine models," *Int. J. Cancer*, 67:842-848, 1996.

(Continued)

*Primary Examiner*—Shin-Lin Chen

(57) ABSTRACT

Methods and pharmaceuticals for inhibiting or preventing metastasis formation in animals, including humans, having primary tumors, through the administration of phosphorothioates including their thiol and disulfide metabolites are disclosed. These compounds stimulate angiostatin levels, inhibit matrix metalloproteinases (MMPs), and stimulate manganese superoxidase dismutase (MnSOD). Phosphorothioates, of which amifostine is an example, can be administered as a combination therapy with traditional cancer therapies, including chemotherapy, radiotherapy, surgery, immunotherapy, hormone therapy and gene-therapy. Inhibition or prevention of metastasis by phosphorothioates is independent of tumor type, including adenocarcinomas and sarcomas.

14 Claims, 6 Drawing Sheets

OTHER PUBLICATIONS

Fink et al., "Design and synthesis of thiol containing inhibitors of matrix metallaproteinases," *Bioorg. Med. Chem. Lett.* 9:195-200, 1999.

Freskos et al., "Discovery of a novel series of selective MMP inhibitors: identification of the γ-fulfone-thiols," *Bioorg. Med. Chem. Lett.*, 9:943-948, 1999.

Gately et al., "Human prostate carcinoma cells express enzymatic activity that converts human plasminogen to the angiogenesis inhibitor, angiostatin," *Cancer Res.*, 56:4887-4890, 1996.

Gately et al., "The mechanism of cancer-mediated conversion of plasminogen to the angiogenesis inhibitor angiostatin," *Proc. Natl. Acad. Aci. USA*, 94:10868-10872, 1997.

Gilbert, "Redox control of enzyme activities by thiol/disulfide exchange," *In: Methods in Enzymology*, Academic Press, New York, 107:330-351, 1984.

Grdina et al., "Thiol and disulfide metabolites of the radiation protector and potential chemopreventive agent WR-2721 are linked to both its anti-cytotoxic and anti-mutagenic mechanisms of action," *Carcinogenesis*, 16:767-774, 1995.

Grdina et al., "Chemopreventive doses of Amifostine confer no cytoprotection to tumor nodules growing in the lungs of mice treated with cyclophosphamide," *Sem. Oncol.*, 26: 22-27, 1999.

Grdina et al., "Protection against late effects of radiation by s-2-(3-aminopropylamino)-ethylphosphorothioic acid," *Cancer Research*, 51:4125-4130, 1991.

Grdina et al., "The radioprotector WR-2721 reduces neutron-induced mutations at the hypoxanthine-guanine phosphoribosyl transferase locus in mouse splenocytes when administered prior to or following irradiation," *Carcinogenesis*, 13: 811-814, 1992.

Hirschel-Scholz et al., "Interference of WR-2721 with magnesium metabolism: mechanism of action," *Miner Electrolyte Metab.*, 14:114-20, 1988.

Hoffman et al., "Would fluid from venous leg ulcers degrades plasminogen and reduces plasmin generation by keratinocytes," *J. Invest Dermatol.*, 111:1140-1144, 1998.

Kahari et al., "Matrix metalloproteinases and their inhibitors in tumor growth and invasion," *Ann. Med.*, 31:34-45, 1999.

Kanclerz and Chapman, "Influence of misonidazole, sr-2508, rsu-1069 and wr-2721 spontaneous metastases in c57bl mice," *Int J Radiat Oncol Biol Phys*, 14:309-316, 1988.

Kataoka et al., "Anti-mutagenic effects of amifostine: clinical implications," *Semin. Oncol.*, 23:53-57, 1996.

Kataoka et al., "Anti-mutagenic effects of the radioproctector WR-2721 against fission spectrum neutrons and $^{60}$Co γ-rays in mice," *Int. J. Radiat. Biol.*, 61:387-392, 1992.

Kleiner et al., "Matrix metalloproteinases and metastasis," *Cancer Chemother. Pharmacol.*, 43:S42-S51, 1999.

Langeland et al., "Metal binding properties of thiols; complexes with horse liver alcohol dehydrogenase," *Comp, Biochem. Physiol Part B*, 123: 155-162, 1999.

Li et al., "Overexpression of manganese superoxide dismutase in DU145 human prostate carcinoma cells has multiple effects on cell phenotype," *Prostate*, 35:221-233, 1998.

Liu et al., "Repression of c-myc gene expression by the thiol and disulfide forms of the cytoprotector amifostine," *Carcinogenesis*, 18:2457-2459, 1997.

Liu et al., "Transfection and expression of MnSOD cDNA decreases tumor malignancy of human oral squamous carcinoma SCC-25 cells," *Human Gene Ther.*, 8:585-595, 1997.

Llobert et al., "Comparative effects of repeated parenteral administration of several chelators on the distribution and excretion of cobalt," *Res. Comm. Chem. Path, Pharmacol.*, 60(2):255-233, 1988.

McDonnell et al., "Zinc ejection as a new rationale for the use of a cystamine and related disulfide-containing antiviral agents in the treatment of AIDS," *J. Med. Chem.*, 40:1969-76, 1997.

Milas et al., "Inhibition of radiation carcinogenesis in mice by S-2-(3-aminopropylamino) ethylphosphorothioic acid," *Cancer Res.*, 44:5567-5569, 1984.

Milas et al., "Effect of tumor type, size, and endpoint on tumor radioprotection by WR-2721," *Int. J. Radiat. Oncol. Biol. Phys.*, 10:41-48, 1984.

Oku et al., "Antimetastatic and antitumor effect of a recombinant human tissue inhibitor of metalloproteinases-2 in murine melanoma models," *Biol Pharm Bull*, 20:843-849, 1997.

Penhaligon "Radioprotection of mouse skin vasculature and the RIF-1 fibrosarcoma by WR-2721," *Int. J. Radiat. Oncol. Biol. Phys.*, 10:1541-1544, 1984.

Pinkus et al., "Role of oxidants and antioxidants in the induction of AP-1, NFkB, and glutathione S-transferase gene expression," *J. Biol. Chem.*, 271:13422-13429, 1996.

Polla et al., "Protection from cellular oxidative injury and calcium intrusion by n-(2-mercaptoethyl)-1, 3-propanediamine, WR 1065," *Biochem. Pharmacol.*, 40: 1469-1475, 1990.

Prontera et al., "Inhibition of gelatinase A (MMP-2) by batimastat and captopril reduces tumor growth and lung metastases in mice bearing lewis lung carcinoma," *Int. J. Cancer*, 81:761-766, 1999.

Sack et al., "Diurnal variations in angiostatin in human tear fluid: a possible role in prevention of corneal neovascularization," *Curr. Eye Res.*, 18:186-193, 1999.

Safford et al., "Suppression of fibrosarcoma metastasis by elevated expression of Manganese Superoxide Dismutase," *Cancer Res.*, 54:4261-4265, 1994.

Sen, "Redox signaling and the emerging therapeutic potential of thiol antioxidants," *Biochem. Pharmacol.*, 55: 1747-1758, 1998.

Spencer, C.M. et al., "A review of its pharmacodynamic and pharmacokinetic properties, and therapeutic potential as a radioprotector and cytotoxic chemoprotector," *Drugs*, 50: 1001-1031, 1995.

Stack et al., "Angiostatin inhibits endothelial and melanoma cellular invasion by blocking matrix-enhanced plasminogen activation," *Biochem J.*, 340:77-84, 1999.

Stathakis et al., "Angiostatin formation involves disulfide bond reduction and proteolysis in kringle 5 of plasmin," *J. Biol. Chem.*, 274(13):8910-8916, 1999.

Stathakis et al., "Generation of angiostatin by reduction and proteolysis of plasmin," *J. Biol. Chem.*, 272:20641-20645, 1997.

Stewart et al., "Radioprotection of two mouse tumors by WR-2721 in single and fractionated treatments," *Int. J. Radiat. Oncol. Biol. Phys.*, 9:507-513, 1983.

Volpert et al., "Captopril inhibits angiogenesis and slows the growth of experimental tumors in rats," *J. Clin. Invest.*, 98:671-679, 1996.

Woloschak et al., "Expression of thymidine kinase messenger RNA and a related transcript is modulated by the radioprotector WR-1065," *Cancer Res.*, 55:4788-4792, 1995.

\* cited by examiner

Human Glioma Cells

SH - active thiol form of amifostine; TNF - tumor necrosis factor alpha; L-NAC - N-acetyl-L-cysteine
D-NAC - N-acetyl-D-cysteine; EDTA - ethylenediaminetetraacetic acid

METHOD FOR PROTECTION AGAINST TUMOR METASTASIS FORMATION

This application claims priority to U.S. Provisional Application Ser. No. 60/125,605 filed on Mar. 19, 1999.

The government may own rights in the present invention pursuant to grant number CA37435-13 from the National Institutes of Health.

BACKGROUND OF THE INVENTION

1. Field of the Invention

The present invention is generally directed to the fields of cancer biology and biochemistry. More particularly, the present invention is directed to a method for inhibiting the formation of metastases from primary tumors growing in mammals.

2. Description of Related Art

As cancer treatments using radiation and/or chemotherapies become more effective, and more people live for longer periods of time following treatment, cancer survivors are faced with a significant risk of developing therapy-induced secondary tumors (P. Y. Leverger et al., 1998; B. E. Johnson, 1998; J. E. Karp et al., 1997; S. Bhatia et al., 1996). Because of the inherent mutagenicity of ionizing radiation and most anti-cancer drugs, investigators as early as 1978 predicted that therapy-induced secondary tumors would become a major health issue (T., Sugimura et al., 1978). This is most evident in the treatment of children and young adults having potentially curable cancers such as Hodgkin's disease. It has been reported that women, treated for Hodgkin's disease in their teens with radiation and chemotherapy, had a 75-fold increased risk for the development of breast cancer by age 40, as compared to matched control populations. The estimated actuarial cumulative probability of breast cancer development in this population was 35% (S. Bhatia et al., 1996). The issue of therapy-induced secondary cancers could be effectively addressed if novel anti-cancer agents lacking mutagenic and carcinogenic properties could be identified and developed. This approach, however, is not at present either practical or feasible. A much more reasonable approach is the addition of agents that do not affect therapeutic efficacy but do possess anti-mutagenic and anti-carcinogenic properties to standard cancer therapies involving radiation and cytotoxic drugs.

The application of agents to inhibit the carcinogenic process in cells is defined as chemoprevention (M. A. Morse et al., 1993; G. J. Kelloff et al., 1994; A. J. Alberg et al. 1998). Chemoprevention is a broad term that encompasses the prevention of cancer in high-risk disease-free individuals; inhibition of second primary tumors induced by chronic exposure to carcinogens due to high risk life styles, i.e., the field cancerization process (W. K. Hong et al., 1997); and the prevention of new cancers in patients having a good prognosis for cure but who are at risk of developing therapy-induced secondary tumors. Chemoprevention applied to the first two groups generally involves the chronic administration of low levels of anti-carcinogenic agents with the intention of inhibiting both the initiation and progression steps of the carcinogenic process (F. L. Meyskens, Jr., 1991). Application of chemoprevention to the third group is somewhat different from that of the first two groups in that patients already will have cancer, have a good prognosis, and are exposed to known doses of highly carcinogenic therapeutic agents such as ionizing radiation and chemotherapeutic drugs. In this group, the chemopreventive agent can be administered as an acute dose at the time of therapy to reduce the probabilities of initiation and early promotional events involved in the therapy-induced carcinogenic process. However, since the target population for this approach are patients having a good prognosis for cure, it is essential that the chemopreventive agents used do not diminish therapeutic efficacy or enhance tumor spread and metastases formation.

While a large number of drugs have been clinically studied, thiol-containing compounds appear to represent an effective class of agents for use in chemoprevention. The thiol N-acetyl-L-cysteine (L-NAC) has been clinically evaluated both in Europe (project Euroscan) and the U.S. (National Cancer Institute) as a chemopreventive agent capable of inhibiting carcinogenesis (S. De Flora et al., 1995) and mutagenesis (S. De Flora et al., 1985). Likewise, the synthetic dithiolthione oltipraz (4-methyl-5-pyrazinyl-3H-1,2-dithiol-3-thione) has been clinically investigated as a chemopreventive agent (A. B. Benson, III, 1993; W. Kim et al., 1997) and found to be effective in inhibiting both the initiation and progression stages of carcinogenesis (G. J. Kelloff et al., 1994). Both L-NAC (S. De Flora et al., 1985) and oltipraz (P. C. Hayes et al., 1991; T. W. Kensler et al., 1995) also were found to increase intracellular glutathione (GSH) levels in exposed cells and to independently activate nuclear transcription factor κB (NFκB) and subsequent gene expression and enzyme activity of manganese superoxide dismutase (MnSOD) (K. C. Das et al., 1995; J., Antras-Ferry et al., 1997). Amifostine (S-2-[3-aminopropylamino] ethylphosphorothioic acid; also referred to as WR-2721) is in clinical use as a cytoprotective drug to minimize radiation and/or chemotherapeutic toxicity to normal tissues in patients treated by high dose cisplatin for ovarian cancer (R. T. Dorr, 1998; J. A. Foster-Nora et al., 1997; C. M. Spencer et al., 1995). In preclinical studies, this drug and its active thiol metabolite WR-1065 (2-[{aminopropyl}amino] ethanethiol) were found to be anti-carcinogenic (L. Milas et al., 1984; B. A. Carnes et al., 1992) and anti-mutagenic (Y. Kataoka et al., 1992; D. J. Grdina et al., 1992; Y. Kataoka et al., 1996) and capable of activating NFκB and MnSOD gene expression.

Cytoprotection is the use of a chemical agent to prevent cell killing and/or loss of function in dose limiting normal tissues exposed to radiation and/or chemotherapy during the treatment of cancer. Since the magnitude of cytoprotection obtained is dose dependent, maximum tolerated doses of cytoprotective agents are routinely administered during cancer treatment for the protection of normal tissues. This approach is only appropriate if it can be shown that enhanced cytoprotection is selectively limited to only normal as compared to malignant cells and tissues. Amifostine is currently limited for use in the clinic by the FDA to only patients who are not expected to enjoy a significant survival benefit or cure from their chemotherapy (Package insert for Ethyol®, 1997; News and Product Notes, 1996). The basis for this restricted use of amifostine as a cytoprotector is based on early studies with animal models. It was demonstrated that large cytoprotective doses of amifostine could protect animal tumors to a similar magnitude as reported for normal tissues, i.e., protection factors of 1.2 to 2.5 (L. Milas et al. 1984; J. S. Rasey et al., 1986; F. A. Steward et al., 1983; M. Penhaligon, 1984; S. L. McChesney et al., 1986). It has been demonstrated that there is a threshold dose of amifostine below which no cytoprotection can be demonstrated in either normal or malignant cells (D. J. Grdina et al., 1995; Y. Kataoka et al., 1996; D. J. Grdina et al., 1999). Maximum cytoprotection in the C3H mouse system requires an amifostine dose of 400 mg/kg while doses below 100 mg/kg are completely ineffective (L. Milas et al., 1984; Kataoka et al., 1996; D. J. Grdina et al., 1999). In contrast, chemopreventive doses of amifostine required to prevent radiation-induced mutations at the hprt locus in splenocytes in these mice ranged from as low as 25 mg/kg to a high of 400 mg/kg, with the effect diminishing only at doses less than 10 mg/kg (D. J. Grdina et al., 1992). These data highlight the fundamental difference implicit in the design of studies to evaluate the use of thiols in chemoprevention as compared to cytoprotection. Chemoprevention focuses on determining the minimum concentration of thiol required to afford only prevention of therapy-induced mutations and inhibition of carcinogenic processes.

Previous applications have defined these roles for phosphorothiorates and their corresponding thiols, when administered at low and non-cytoprotective doses, in preventing radiation-induced mutations in nonmalignant cells (i.e., chemoprevention). Chemicals of the phosphorothioate genus and associated metabolites can protect against somatic mutations when administered to mammals following a mutagen exposure, as detailed in U.S. Pat. Nos. 5,567,686; 5,488,042, and 5,891,856, which are herein specifically incorporated by reference in their entirety. This protection is irrespective of the nature of the mutagenic event or source of radiational or chemical insult, as detailed in U.S. Pat. No. 5,869,338, which is incorporated by reference in its entirety.

In addition to their anti-mutagenic properties, these thiols have been reported to be effective at inhibiting tumor cell growth under both in vitro and in vivo experimental conditions. As early as 1975, it was reported that cysteamine could inhibit the growth of five different transplanted tumors in mice. The largest effect was observed when it was administered to test animals at the time of tumor-transplantation (C. A. Apffel et al., 1975). The thioglycerol (i.e., lacking a terminal amino group) and mercaptopropylamine (i.e., 3-carbon homologue of cysteamine) were significantly less effective than cysteamine while cystamine (i.e., the disulfide form of cysteamine) was completely ineffective in inhibiting tumor growth. This led to the conclusion that both active thiol and amino groups are required for the maximum inhibitory effect on tumor cell growth. The ability to inhibit tumor growth also has been reported for NAC (S. De Flora et al., 1996).

One major limitation of general cancer strategies is the inability to inhibit or eradicate metastasis. It is well recognized that metastatic spread of disease is a poor prognostic factor for the treatment of human cancer. To date, strategies designed to attack the metastases problem focus only on the development of cytotoxic drugs and treatments to kill metastases that have already escaped the primary tumor site. There exists a need for a method for protecting against the formation of metastases from primary tumors growing in mammals, irrespective of the cancer therapy, which will be amenable to pre- and/or post cancer therapy administration and which will be optimally effective at non-toxic concentrations so as to allow use in mammals and also allow for multiple, as well as single, administrations.

SUMMARY OF THE INVENTION

Accordingly, it is the object of the present invention to provide a novel method for reducing the number or incidence of metastases in an animal, including humans, exhibiting a primary tumor comprising administering to said animal a subcytoprotective dose of a phosphorothioate or active metabolite thereof. Doses of the phosphorothioate or active metabolite range from about 10 mg/kg to about 150 mg/kg, to about 200 mg/kg or to about 400 mg/kg. A "subcytoprotective dose" refers to an amount that is too low to prevent cell killing and/or loss of function in normal tissues exposed to radiation and/or chemotherapy. A "non-cytoprotective dose" refers to an amount that is unable to prevent cell killing and/or loss of function in normal tissues exposed to radiation and/or chemotherapy. The phrase "active metabolite" is used according to its ordinary meaning among those of skill in the art, i.e., to refer to a product of intermediary metabolism that possesses an activity.

It is an aditional object of the present invention to provide a novel method for reducing the number of metastases in an animal, including humans, exhibiting a primary tumor comprising administering to said animal a subcytoprotective dose of a phosphorothioate, wherein said compound is an aminoalkylphosphorothiate compound or its active thiol or disulfide derivative form.

It is a further object of the present invention to provide a novel method for reducing the number of metastases in an animal, including humans, exhibiting a primary tumor comprising administering to said animal a subcytoprotective dose of a phosphorothioate or active metabolite thereof, wherein said compound is selected from the group consisting of WR-2721 (amifostine), WR-1065, WR-638, WR-77913, WR-33278, WR-3689, WR-2822, WR-2529, WR-255591, WR-2823, WR-255709, WR-151326 and WR-151327.

Accordingly, it is the object of the present invention to provide a therapeutic route and formulation for reducing the number of metastases in an animal, including humans, exhibiting a primary tumor comprising administering to said animal a subcytoprotective dose of a phosphorothioate or active metabolite thereof, wherein said compound's route of administration is intravenous, intraperitoneal, intradermal, intramuscularoral, dermal, nasal, buccal, rectal, vaginal, inhalation, or topical or wherein said compound is formulated into solutions, suspensions, tablets, pills, capsules, sustained release formulations, powders, creams, ointments, salves, sprays, pumps, liposomes, suppositories, inhalers, and patches.

It is a final object of the present invention to provide a novel method for reducing the number of metastases in an animal, including humans, exhibiting a primary tumor comprising administering to said animal a subcytoprotective dose of a phosphorothioate or active metabolite thereof in combination with at least one other cancer therapy, including chemotherapy, radiotherapy, immunotherapy, hormone therapy, surgery and/or gene therapy.

In some embodiments of the present invention, a method for reducing the number of metastases in an animal with a tumor is effected by administering a subcytoprotective dose of a phosphorothioate, or active metabolite thereof, and then monitoring the ability of that dose to reduce metastases in the animal. Monitoring may be implemented in a number of ways including: measuring the level of angiostatin stimulation; measuring the activity level of a matrix metalloproteinase, such as MMP-2 or MMP-9; and measuring the level of stimulation of MnSOD, for example, by assaying the stimulation of MnSOD gene expression.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
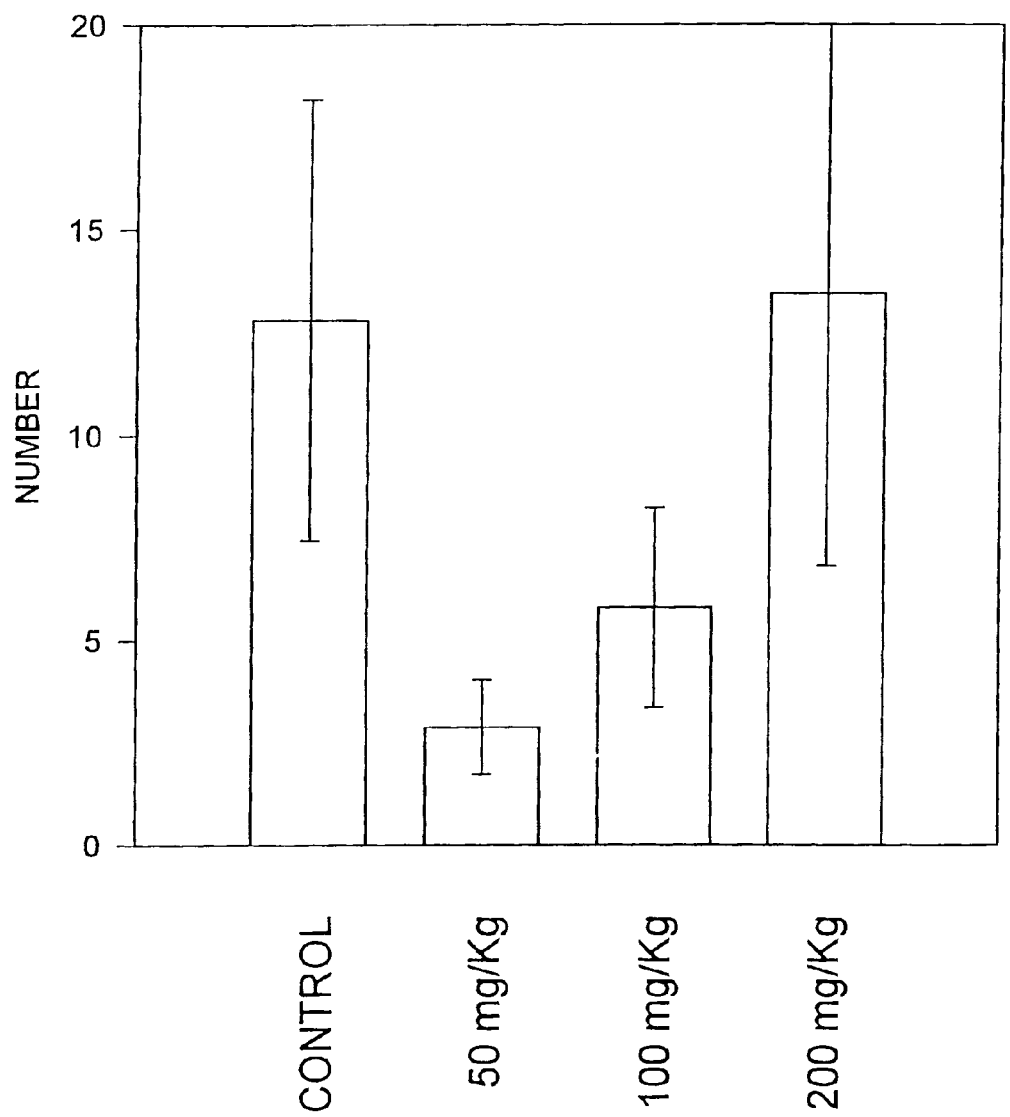
FIG. 1. Amifostine Effect on Metastases Formation. Mice were injected intraperitoneally with 200, 100, or 50 mg/kg of WR-2721, showing that amifostine reduces the chances of developing spontaneous metastases, especially at lower concentrations.

Several therapies have been developed to treat cancer, including chemotherapy, radiotherapy, surgery, and genetherapy. One major limitation of these cancer strategies is the inability to inhibit or eradicate metastasis. It is well recognized that metastatic spread of disease is a poor prognostic factor for the treatment of human cancer. To date, strategies designed to attack the metastases problem focus only on the development of cytotoxic drugs and treatments to kill metastases that have already escaped the primary tumor site. There exists a need for a method for protecting against the de novo formation of metastases from primary tumors growing in mammals, irrespective of the cancer therapy.

Cytoprotection is the use of a chemical agent to prevent cell killing and/or loss of function in normal tissues exposed to radiation and/or chemotherapy during the treatment of cancer. Since the magnitude of cytoprotection obtained is dose dependent, maximum tolerated doses of cytoprotective agents are routinely administered during cancer treatment for the protection of normal tissues. This approach is only appropriate if it can be shown that enhanced cytoprotection is selectively limited to only normal as compared to malignant cells and tissues. Amifostine is currently limited for use in the clinic by the FDA to only patients who are not expected to enjoy a significant survival benefit or cure from their chemotherapy (Package insert for Ethyol®(g, 1997; News and Product Notes, 1996). The basis for this restricted use of amifostine as a cytoprotector is based on early studies with animal models. A description of cytoprotection and methods of assaying for cytoprotection are provided in U.S. Pat. Nos. 5,567,686; 5,488,042, 5,891,856, and 5,869,338.

Phorphorothioates and their corresponding thiols, of which amifostine is an example, when administered at low and non-cytoprotective doses, also have been shown to be useful in preventing radiation-induced mutations in nonmalignant cells (i.e., chemoprevention). Chemicals of the phosphorothioate genus and associated metabolites can protect against somatic mutations when administered to mammals following a mutagen exposure, irrespective of the nature of the mutagenic event or source of radiational or chemical insult.

The present application demonstrates, for the first time, that chemicals of the phosphorothioate designation and their associated metabolites can also reduce metastatic tumor formation in an animal exhibiting a primary tumor. Reduction of metastatic tumor formation optimally occurs at low concentrations, less than concentrations needed for protection against cell lethality. Higher concentrations of phosphorothioates and their associated metabolites also may be beneficial in reducing metastatic tumor formation. The reduction in metastatic tumor formation is a general property of phosphorothioates and their associated metabolites, as exemplified by S-2-(3-aminopropylamino)ethyl phosphorothioic acid (amifostine, WR-2721) and its corresponding thiol and disulfide metabolites. This represents a novel use of phosphorothioates and their associated metabolites in the treatments of human cancers.

Amifostine and its thiol and/or disulfide metabolites inhibit spontaneous metastasis formation in rodent animal models. The mechanisms of action that can account for this effect include: 1) the stimulation of angiostatin production in animals with or without tumors which leads to the inhibition of angiogenesis and therefore inhibits the necessary blood supply required for metastasis development; 2) the inhibition of matrix metalloproteinases which are zinc containing enzymes required for tumor cell invasion of normal tissues; and 3) the stimulation of manganese superoxide dismutase (MnSOD) expression in tumor cells which in turn leads to a loss or reduction of their malignant phenotype.

The mechanism of angiostatin stimulation involves the interaction of urokinase with a sulfhydryl doner such as WR-1065, the free thiol form of amifostine and plasminogen (Gately et al., 1997; Stathakis et al., 1997). Contrary to the present art, the presence of a tumor as the source of urokinase is not required for the production of angiostatin. This is important because primary solid tumors produce angiostatin to inhibit new metastatic growth. Once the primary tumor is removed surgically angiostatin production is no longer evidenced and presumably metastatic grown can be accelerated.

Matrix metalloproteinases (MMPs) are zinc-containing enzymes that are secreted by tumor cells to facilitate invasion and growth in normal tissues. Phosphorothioates, their thiols, and disulfides can chelate metals such as zinc and thus inhibit zinc-containing enzymes (Kleiner et al., 1999; Dijkwel et al., 1986).

Finally, manganese superoxide dismutase (MnSOD) has been identified as important anti-oxidant gene whose expression reduces the malignant/metastatic phenotype of cancer cells (Safford et al., 1994; Urano et al., 1995). Tumor cells are relatively lower in MnSOD than are normal cells.

Phosphorothioates such as amifostine, along with their thiol and disulfide metabolites, inhibit spontaneous metastasis formation at relatively low doses by stimulating high levels of angiostatin following surgical removal of tumors to prevent angiogenesis and metastasis formation; inhibiting tumor cell secreted MMP enzymes that required for tumor cells to invade normal tissues and form metastasis; and enhance MnSOD gene expression in tumor cells that leads to a loss of their malignant phenotype and metastatic ability. The inhibition of metastasis formation is consistent with each and/or all of these amifostine-mediated effects. The enhanced effect at low doses of amifostine is consistent with data that suggests these thiol-containing compounds affect gene expression and enzyme activity by altering the redox environment of the cell. At very low concentration levels of amifostine, there is an insufficient amount of amifostine to initiate a redox-driven reaction. At very high concentrations, amifostine molecules start to react with each other and inhibit the reaction. In contrast to cytoprotection, at intermediate concentrations the redox windows for metastasis prevention are much lower than that required for cytoprotection.

I. Chemical Structures

A general description of the class of compounds and their properties described in this application can be found in Sweeney, 1979 and Giambarresi and Jacobs, 1987, both of which are incorporated by reference. Specific compounds and designations described in this application are as follows: S-2-(3-aminopropylamino)ethyl phosphorothioic acid (amifostine, WR-2721), 2-[(aminopropyl)amino]ethanethiol (WR-1065), S-1-(aminoethyl)phosphorothioc acid (WR-638), S-[2-(3-methylaminopropyl)aminoethyl]phosphorothioate acid (WR-3689), S-2-(4-aminobutylamino)ethylphosphorothioic acid (WR-2822), 3-[(2-mercapto ethyl)amino]propionamide p-toluenesulfonate (WR-2529), S-1-(2-hydroxy-3-amino)propyl phosphorothioic acid (WR-77913), 2-[3-(methylamino)propylamino]ethanethiol (WR-255591), S-2-(5-aminopentylamino)ethyl phosphorothioic acid (WR-2823), [2-[(aminopropyl)amino]ethanethiol]N,N,'-dithiodi-2,1-(ethanediyl)bis-1,3-propanediamine (WR-33278), 1-[3-(3-aminopropyl)thiazolidin-2-Y1]-D-gluco-1,2,3,4,5 pentane-pentol dihydrochloride (WR-255709), 3-(3-methylaminopropylamino)propanethiol dihydrochloride (WR-151326), and S-3-(3-methylaminopropylamino)propyl phosphorothioic acid (WR-151327).

II. Cancer and Therapies for Metastasis

The present invention involves the delivery of therapeutic compounds to individuals with cancer cells to reduce or inhibit metastasis. Target cancer cells include cancers of the lung, brain, prostate, kidney, liver, ovary, breast, skin, stomach, esophagus, bone, pancreas, gum, tongue, head and neck, testicles, colon, gastrointestine, cervix, lymphatic system and blood. Of particular interest are non-small cell lung carcinomas including squamous cell carcinomas, adenocarcinomas, large cell undifferentiated carcinomas, sarcomas and lymphoreticular tumors such as lymphomas and leukemias.

According to the present invention, one may treat the metastasis by direct injection of a tumor or its vasculature with the therapeutic compound. Alternatively, the tumor may be infused or perfused with the therapeutic compound using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

An exemplary course of treatment, for a primary tumor or a post-excision tumor bed, could involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

A. Combination Therapies

Cancer therapies also include a variety of combination therapies with both chemical-, radiation-, surgery-, immune system-, hormone-, and gene-therapy-based treatments.

1. Chemotherapy

Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

2. Radiotherapy

Radiotherapies include what are commonly known as γ-rays, X-rays, high energy-electrons, -protons, or -neutrons, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

4. Immunotherapy

Immunotherapy, a rapidly evolving area in cancer research, is yet another option for the treatment of certain types of cancers. For example, the immune system identifies tumor cells as being foreign and thus they are targeted for destruction by the immune system. Unfortunately, the response typically is not sufficient to prevent most tumor growths. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis*, *Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Edward and Villaseca, 1998; U.S. Pat. No. 5,830,880 and U.S. Pat. No. 5,846,945) and monoclonal antibodies (e.g., anti-ganglioside GM2, anti-HER-2, anti-p 185) (Pietras et al., 1998; Hanibuchi et al., 1998; U.S. Pat. No. 5,824,311).

5. Hormone Therapy

The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

6. Gene Therapy

Several gene therapy approaches to treating cancers are contemplated in combination with phosphorothioate treatment. In order to mediate the effect of transgene expression in a cell, it will be necessary to transfer the therapeutic expression constructs into a cell. Trangenes commonly employed for cancer gene-therapy can be inhibitors of cellular proliferation or regulators of programmed cell death. These transgenes may be selected from the group consisting of tumor suppressors, tumor associated genes, growth factors, growth-factor receptors, signal transducers, hormones, cell cycle regulators, nuclear factors, transcription factors and apoptotic factors. Transgenes that induce or downregulate any members of this group can also be employed in cancer gene-therapy protocols.

7. Exemplary Treatment Regimen

Various combinations may be employed. For example, phosphorothioate is "A" and the radio- or chemotherapeutic or gene-therapy agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

The terms "contacted" and "exposed," when applied to a cell, are used herein to describe the process by which a phosphorothioate and a chemotherapeutic, radiotherapeutic, immunotherapeutic, hormone, or gene therapeutic agent are delivered to a target cell or are placed in direct juxtaposition with the target cell. To achieve cell killing or stasis, both agents are delivered to a cell in a combined amount effective to kill the cell or prevent it from dividing.

III. Pharmaceutical Compositions and Routes of Administration

Aqueous compositions of the present invention comprise an effective amount of the therapeutic compound, further dispersed in pharmaceutically acceptable carrier or aqueous medium. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Where clinical application of liposomes containing therapeutic compounds is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired. An effective dose is understood to refer to an amount necessary to achieve a particular effect, for example, a reduction in metastases. In the practice of the present invention, it is contemplated that doses in the range from 10 mg/kg to 200 mg/kg can effect a reduction in metastases without a concomitant cytoprotection effect. Thus, it is contemplated that doses include doses of about 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200 mg/kg. Furthermore, such doses can be administered at multiple times during a day, and/or on multiple days, weeks, or months.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

It will be understood by those skilled in the art and made aware of this invention that dosage units of mg/kg of body weight can be converted and expressed in comparable concentration units of micrograms/ml or mM (blood levels). It is also understood that uptake after is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, afficacies and results described herein. By way of example only, in mice given 100 mg/kg WR-2721, 30-minute blood levels are reported at 49 micrograms/ml or 0.23 mM. Accordingly, a 400 mg/kg dose would correspond to a concentration of WR-2721 of about 1.0 mM. Likewise, a human subject given about 740 mg/m$^2$ of WR-2721 (by IV infusion) would have an initial plasma level at about 100 micromol/liter or 0.1 mM.

Transfer of transgenes may employ viral or non-viral methods of gene transfer. Expression constructs encoding therapeutic agents may be transferred via viral transduction using infectious viral particles, for example, by transformation with an adenovirus vector. Alternatively, retroviral, adeno-associated virus or bovine papilloma virus may be employed, all of which permit permanent transformation of a host cell with a gene(s) of interest. Other viral vectors may be employed as expression constructs in the present invention. Vectors derived from viruses such as vaccinia virus (Ridgeway, 1988; Baichwal and Sugden, 1986; Coupar et al., 1988), canary pox virus, and herpes viruses may be employed.

Several non-viral methods for the transfer of expression constructs into cultured mammalian cells are contemplated for cancer gene therapy in combination with phosphorothioates. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Methods
  A. In Vitro Methods
  1. Cell Lines and Culture Conditions
  Two different tumor cell systems have been examined from a group of two adenocarcinoma lines (MCa-K and OCa-I) and one sarcoma lines (SA-NH). These tumor lines were chosen for study based on their propensity to form spontaneous metastases in the lungs of mice (J. P. Volpe et al., 1985; R. Schimming et al., 1999; J. P. Volpe et al., 1998; J. P. Volpe et al., 1990; B. W. Brown et al., 1992). Tumor cells are maintained in modified McCoy's 5A medium (Gibco/BRL) supplemented with 20% FBS, penicillin and streptomycin (N. Suzuki et al., 1977). Minor modifications will be made as needed for all tumors (G. L. Nicolson et al., 1991). All cell cultures are grown in a humidified atmosphere at 37° C. with 5% $CO_2$.

2. Chemical Compound Sources

WR-2721 and WR-1065 are supplied by the Drug Synthesis and Chemistry Branch, Division of Cancer Treatment, National Cancer Institute. These agents are made up at a 1 M concentration in phosphate-buffered saline, pH 7.2 (Gibco.BRL) and sterilized by filtration immediately before use.

B. In Vivo Methods

Animal system and experimental tumors. Experiments have been performed using C3Hf/Kam mice obtained from the University of Texas M.D. Anderson Cancer Center, Houston, Tex. Male mice were at least 110 days of age at the initiation of studies. Studies involving tumors included the use of two syngeneic adenocarcinomas (MCa-K and OCa-I,) and one sarcoma (SA-NH). Tumors were grown in the hind legs or flanks of animals. Single-cell suspensions of $5 \times 10^5$ viable tumor cells prepared from excised tumors were injected into the hind leg (spontaneous metastasis assay) or the lateral tail veins (artificial metastasis assay) of mice to develop pulmonary nodules (D. J. Grdina et al., 1974; D. J. Grdina et al., 1977; N. Suzuki et al., 1977; D. J. Grdina et al., 1978). For the spontaneous metastases studies, each thiol was administered on the first day following tumor cell inoculation, and then every third day until the tumor reaches 8.0 to 8.5 mm in diameter. At that time the tumor bearing leg is amputated and thiols were administered two and four days later. Twenty-three days following amputation, the animals were sacrificed, their lungs removed, fixed in Bouin's solution, and lung metastases counted. For the artificial metastases studies, mice were sacrificed 14 days after tumor cell inoculation and lung metastases counted (D. J. Grdina et al., 1974; D. J. Grdina et al., 1977; N. Suzuki et al., 1977; D. J. Grdina et al., 1978).

Results

Studies were begun using an experimental mouse tumor, SA-NH, which was previously demonstrated to exhibit a high probability of forming spontaneous metastasis in C3Hf/Kam mice (J. P. Volpe et al., 1985). This tumor is p53 wild-type (R. Schimming et al., 1999). A tumor cell suspension containing $5 \times 10^5$ viable SA-NH cells was implanted i.m. into the right thighs of three month old male C3Hf/Kam mice. When tumors grew to 8 to 8.5 mm in diameter, each tumor bearing leg was amputated and the animals were then sacrificed 23 days later to assess both the incidence of mice developing metastases and numbers of spontaneous lung metastases formed per mouse. To assess the effects of amifostine on this process, different groups of mice were injected i.p. with 200, 100, or 50 mg/kg of WR-2721 according to the following protocol: drug administration on the first day following inoculation with tumor cells and then every third day until amputation with a final injection 2 days later. The results of this study are presented in FIG. 1. Amifostine treatment did not enhance the probability of developing spontaneous metastases, but actually reduced it, with the greater effects being evidenced at the lower concentrations tested.

The demonstration that a 50 mg/kg dose of amifostine was the most effective in significantly reducing the formation of spontaneous metastases led to a series of studies involving the sarcoma SA-NH and two additional tumors, the adenocarcinomas MCa-K (p53 mutant) and OCa-I (p53 wild type) (R. Schimming et al., 1999). Since each of these tumors exhibit different growth rates, amputations only occurred when tumors reached 8 mm in diameter and animals were subsequently sacrificed at varying times later to determine the extent of spontaneous metastasis formation in the lungs. Presented in Table 1 is a comparison of the effects of amifostine on the mean number of spontaneous metastases formed in the lungs of mice. Table 2 presents data regarding the effects of amifostine on affecting the incidence of metastasis formation using these tumor systems. The level of significance was determined using a t-test for binomial proportions (Walpole and Myers, 1978). Treatment of animals with 50 mg/kg of amifostine reduced the incidence of spontaneous metastasis development by these tumors at a level of significance of $p<0.025$. Amifostine treatment reduced both the number and the incidence of spontaneous metastases in these animals. OCa-I is a relatively slower growing tumor than the other two and it exhibits a lower propensity to form metastases (J. P. Volpe et al., 1988; J. P. Volpe et al., 1990; B. W. Brown et al., 1992).

TABLE 1

Effect of 50 mg/kg WR-2721 on the number of spontaneous metastases for Sa-NH, MCaK, and OCa tumors (mean ± s.e.)

|  | −WR-2721 | +WR-2721 |
| --- | --- | --- |
| Sa-NH | 12.8 ± 5.4 | 2.9 ± 1.1 |
| MCaK | 16.8 ± 16.1 | 1.7 ± 1.3 |
| OCa | 1.3 ± 0.35 | 0.5 ± 0.14 |

TABLE 2

Effect of 50 mg/kg WR-2721 on incidence of spontaneous metastases for Sa-NH, MCaK, and OCa tumors

|  | −WR-2721 | +WR-2721 |
| --- | --- | --- |
| Sa-NH | 23/30 (77%) | 23/40 (57%) |
| MCaK | 8/16 (50%) | 6/19 (32%) |
| OCa | 12/24 (50%) | 11/30 (37%) |

These examples describe in a systematic manner the effects of phosphorothioates, at low non-cytoprotective doses, on the metastatic process(es). The underlying hypothesis is that anti-oxidant thiols will affect intracellular reduction-oxidation (redox) states that in turn alter gene expression (R. Pinkus et al., 1996; G. E. Woloschak et al., 1995), synthesis of intra-cellular thiols (R. D. Issels et al., 1988; P. U. Devi et al., 1990), and enzyme activities (i.e., redox control of sensitive cysteine residues) (H. Gilbert, 1984; S. Tuttle et al., 1998). The oxidation-reduction (redox) based regulation of signal transduction and gene expression is emerging as an important regulatory mechanism in cell biology (R. Pinkus et al., 1996; H. Gilbert, 1984; S. Tuttle et al., 1998; C. K. Sen, 1998). In addition, the polyamine like structure and behavior of the thiol and di sulfide metabolites allow for sequestration of the reactive thiol (SH) and di sulfide (SS) groups to the microenvironment near actively transcribed regions of cellular DNA. Redox sensitive targets will respond differently as the intracellular redox environment of the cell is altered by its exposure to varying levels of exogenously added thiols. This hypothesis is also consistent with the observations that both NAC and amifostine are more effective at lower doses to inhibit metastasis formation (S. De Flora et al., 1996; A. Albini et al., 1995). As thiol concentration increases, the intracellular redox environment will change and again alter gene expression and enzyme activity (R. Pinkus et al., 1996; H. Gilbert, 1984; S. Tuttle et al., 1998; C. K. Sen, 1998). This suggests that these thiol effects on metastases formation are the result of intracellular changes in redox environment and subsequent signal transduction processes and gene expression.

While some of the antimetastatic activities of L-NAC have been previously described (De Flora et al., 1996; Albini et al., 1995), there are some important distinctions between L-NAC and phosphorothioates. L-NAC requires higher concentrations to work and is driven more by mass action, requiring chronic administration. It is a precursor for glutathione synthesis (GSH) and initiates its biosynthesis. In addition, L-NAC is negatively charged (net charge of −1) while Amifostine has a net positive charge of +2 for its thiol form and +4 for its disulfide form. The positive charges of amifostine's metabolites, in contrast to L-NAC, can account for their relative enhanced attraction and localization with the DNA in the mitochondria and the nucleus (Newton et al., 1996). In these ways, the inherent distinction of amifostine when compared to L-NAC is that it is active at low concentrations of 4 to 40 uM, has polyamine-like activity, is independent of glutathione, and enhances intracellular redox potentials. In this way, amifostine can bind to and stabilize chromatin, enhance the fidelity of repair, alter gene expression (repress c-myc and enhance thymidine kinase), affect enzyme activity (inhibit topoisomerase II activity), and prolong cell cycle transit times. It is proposed that at low doses the disulfide metabolite participates in polyamine driven reactions ultimately leading to changes in gene expression whose consequences then lead to the modification of metastatic processes.

Example 2

Metastatic development results from the exfoliation of viable malignant cells from the primary tumor, their migration to distant sites followed by their invasion into normal organs and tissues and eventual growth to establish new and usually more malignant disease (Zetter, 1998; Ahmad et al., 1997). Three elements of this process are sensitive to thiol exposure and were investigated to confirm the effect of thiols: stimulation of angiostatin, inhibition of the activity of matrix matelloproteinases (MMPs), and up-regulation of manganese superoxide dismutase gene expression.

Phosphorothioates and their thiol and disulfide metabolites inhibit spontaneous metastasis formation at relatively low doses. These phosphorothioates, including amifostine, mediate several different effects: 1) stimulating high levels of angiostatin following surgical removal of tumors to prevent angiogenesis and metastasis formation; 2) inhibiting tumor cell secreted MMP enzymes that required for tumor cells to invade normal tissues and form metastasis; and 3) enhancing MnSOD gene expression in tumor cells that leads to a loss of their malignant phenotype and metastatic ability. The inhibition of metastasis formation is consistent with each and/or all of these amifostine-mediated effects.

Stimulation of Angiostatin

Both primary tumors and metastases require neovascularization to afford the necessary supply of nutrients, growth factors, hormones and oxygen for growth and development (Clement et al., 1999). When angiogenesis is inhibited or reduced, both tumor and metastatic growth decreases significantly (Falcone et al., 1998; Lannutti et al., 1997). An effective inhibitor of angiogenesis and metastatic growth is a 38-kDa internal fragment of plasminogen known as angiostatin (Gately et al., 1996). Angiostatin can be naturally generated following the proteolysis of plasminogen (Stathakis et al., 1997). Two important components of this process have been identified as urokinase and a free sulfhydryl donor to facilitate the reduction of cysteine—cysteine disulfide bonds in kringle 5 of plasmin that then results in a cleavage of the molecule to form angiostatin (Stathakis et al., 1999). Both NAC and captopril were effective as sulfhydryl donors in this reaction resulting in the production of active angiostatin as evidenced by its ability to suppress the growth of Lewis lung carcinoma metastases (Gately et al., 1997). While it was originally proposed that this reaction was dependent upon urokinase secreted by tumors (Gately et al., 1997), angiostatin is also produced under non-malignant conditions (Hoffman et al., 1998; Sack et al., 1999). Amifostine is also effective in inducing angiostatin production in both tumor-free and tumor-bearing mice (see FIG. 2).

Figure 2:
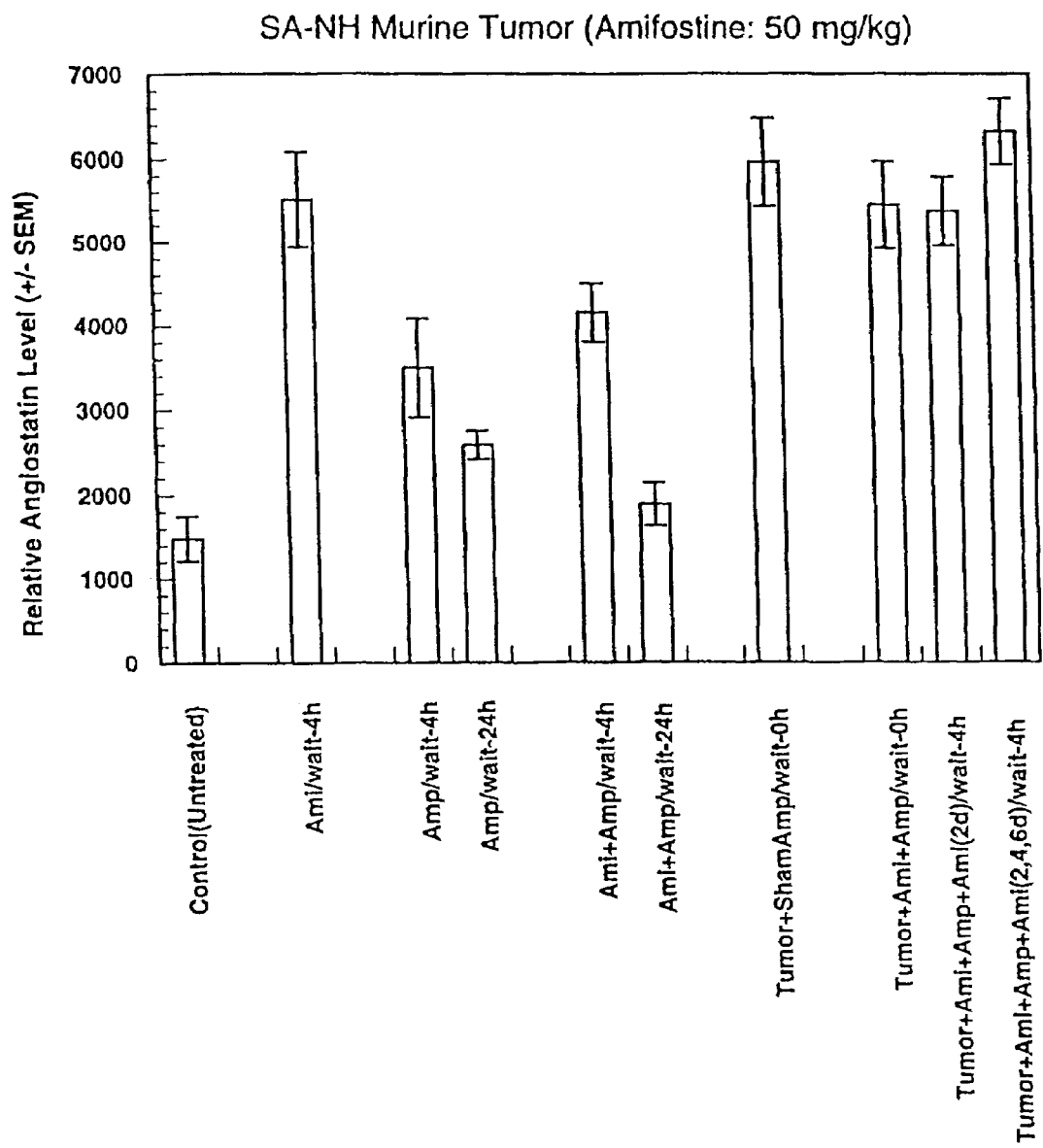
FIG. 2. SA-NH Murine Tumor. Tumor cells ($3-5\times10^5$) were injected into right leg muscle of C3Hf/Kam male mice. Each group consisted of 5 mice. Mice were injected i.p. with 50 mg/kg of Amifostine (Ami) one day after innoculation with viable tumor and every third day (4 times) until amputation (Amp). When tumors grew to 8–9 mm in diameter, the tumor-bearing leg was amputated. Blood was collected using a 1 ml tuberculine syringe rinsed with EDTA (100 mg/ml) or heparin and placed in an EDTA-coated microcentrifuge tube and centrifuged at 250 rpm for 10 min. The resulting supernatants were collected and frozen at $-70°$ C. until assayed for angiostatin by Western blot analysis.

Low non-cytoprotective doses of Amifostine, in the range of 50 to 100 mg/kg, were administered every other day for six days to C3Hf/Kam mice bearing SA-NH sarcomas and twice thereafter following the surgical removal of the tumors. This treatment protocol resulted in a four-fold reduction in the development of spontaneous metastases in the lungs. Amifostine or its free thiol form designated WR-1065 was further evaluated regarding three processes implicated in the metastatic process. (FIG. 2). Amifostine injections resulted in a four-fold enhancement of angiostatin levels found in control mice. Serving as a SH donor to facilitate angiostatin production, continued Amifostine treatment of mice following removal of their tumors resulted in an elevated angiostatin level equal to presurgery levels.

Anti-oxidant thiols can affect intracellular reduction-oxidation (redox) states that in turn alter gene expression (Pinkus et al., 1996; Woloschak et al., 1995), synthesis of intra-cellular thiols (Issels et al., 1988; Deyi et al., 1990) and enzyme activities (i.e., redox control of sensitive cysteine residues) (Gilbert, 1984; Tuttle et al., 1998). The oxidation-reduction (redox) based regulation of signal transduction and the administration of thiols following removal of the tumor will result in the maintenance of high levels of angiostatin, and will therefore exhibit an anti-metastatic effect. Thus, amifostine may be administered both before and after amputation.

Inhibition of MMP Activity

Matrix metalloproteinases (MMP) are a family of enzymes that can degrade the extracellular matrix (Duivenvoorden et al., 1997). MMPs facilitate tumor cell invasion and metastasis formation by at least three distinct mechanisms (Kleiner et al., 1999). First, a proteinase action removes physical barriers to invasion through the degradation of extracellular matrix macromolecules such as collagens, laminins, and proteoglycans. Second, MMPs have the ability to modulate cell adhesion to allow for new cell-matrix and cell—cell interations. Finally, MMPs can act on the extracellular matrix components or other proteins and alter their activities to include even the production of angiostatin.

The human mmp gene family contains at least 16 structurally related members, which can be divided into subgroups of: collagenases, gelatinases, stromelysins, membrane-type MMPs, and novel MMPs (TABLE 3). (Kahari et al., 1999).

TABLE 3

| Collagenases | Gelatinases |
| --- | --- |
| MMP-1 (fibroblast collagenase) | MMP-2 (gelatinase A) |
| MMP-8 (neutrophil collagenase) | MMP-9 (gelatinase B) |
| MMP-13 (collagenase 3) | |
| Stromelysins | MT-MMP |
| MMP-3 (stromelysin-1) | MMP-14 (MT1-MMP) |
| MMP-10 (stromelysin-2 | MMP-15 (MT2-MMP) |
| MMP-11 (stromelysin-3) | MMP-16 (MT3-MMP) |
| MMP-12 (metalloelastase) | MMP-17 (MT4-MMP) |
| MMP-7 (matrilysin) | |
| Novel MMPs | |
| MMP-19 | |
| MMP-20 (enamelysin) | |

In general, MMPs contain a signal peptide, a catalytic domain with a highly conserved zinc-binding site, and a haemopexin-like domain linked to a catalytic domain by a hinge region (Kahari et al., 1999). Three are two key structural motifs that are highly conserved among all of the MMPs, and which set them apart from other metalloproteinases. The first the zinc-binding active site domain, a highly conserved stretch of 50–55 amino acids which contains three histidines occupying three of the coordination sites of the active zinc ion (Lovejoy et al., 1994). The second key structural motif is the conserved sequence in the pro-domain of the protein that contains a cysteine residue which is responsible for maintaining latency in proMMPs by occupying the fourth zinc coordination site with its sulphydryl group (Springman et al., 1990). Activation of proMMPs must, at some point in the mechanism, destabilize and break the zinc-sulfur bond. This is usually followed by cleavage of the cysteine-containing sequence from the now active enzyme (Kleiner et al., 1993).

MMPs are produced by a wide variety of cell types, including epithelial cells, fibroblasts, and inflammatory cells. (Stetler-Stevenson, 1999). With the exception of neutrophil MMPs (neutrophil collagenase and gelatinase B), which are stored in secondary and tertiary granules poised for rapid release, MMP production and activity are highly regulated. Normal tissues do not store MMPs, and constitutive expression is minimal. (Shapiro et al., 1999). MMPs reportedly produced by endothelial cells are MMP-1, MMP-2, MMP-9, and MT1-MMP. There is a considerable body of data indicating that in many common forms of human malignancy then expression and regulation of MMP activity is abnormal. (Brown, 1997).

Development of MMP inhibitors has been ongoing since the 1980s (Brown, 1997). Some MMP inhibitors have shown a range of effects including inhibition of tumor growth. They also exhibit additive anti-tumor effects when combined with cytotoxic chemotherapy drugs (Brown, 1997). Inhibitors of MMP activity have been observed to also be effective inhibitors of metastases formation (Duisenvoorden et al., 1997). Most synthetic inhibitors rely on a functional group to chelate zinc from the active site (Freskos et al., 1999).

Thiols, by virtue of their ability to chelate metals such as zinc, have been identified as an important class of MMP inhibitors (Freskos et al., 1999; Fink et al., 1999; Langeland et al., 1999). This has been demonstrated for NAC (Llobert et al., 1988; Banner et al., 1986; Brumas et al., 1992), captopril (Prontera et al., 1999; Volpert et al., 1996), amifostine (Polla et al., 1990; Hirschel-Scholz et al., 1988), and cystamine (McDonnell et al., 1997). Both NAC (Dorr, 1998; Albini et al., 1995) and captopril (Prontera et al., 1999; Volpert et al., 1996) have been reported to be effective in inhibiting zinc-dependent MMPs, which can be reversed by the addition of $ZnCL_2$ to the culture medium (Volpert et al., 1996).

To extend these observations, amifostine's free thio form (WR-1065) has been evaluated, along with captopril and NAC, with regard to their abilities to inhibit MMPs secreted by human glioma cells. These data are presented in FIGS. 3–5). WR-1065 at a concentration of 40 $\mu$M reduced MMP-2 activity by 45% and MMP-9 by 5% relative to matched controls. A 4 mM concentration of WR-1065 was equally as effective as the well characterized chelating agent EDTA in completely inhibiting both MMP-2 and MMP-9 activity. NAC both the D- and L-isomers, at a concentration of 10 mM inhibited MMP-2 by at least 69%. MMP-9 activity was also inhibited to a similar extent by both isoforms of NAC. Captopril at 10 mM concentration, completely inhibited the activity of both MMPs.

Figure 3:
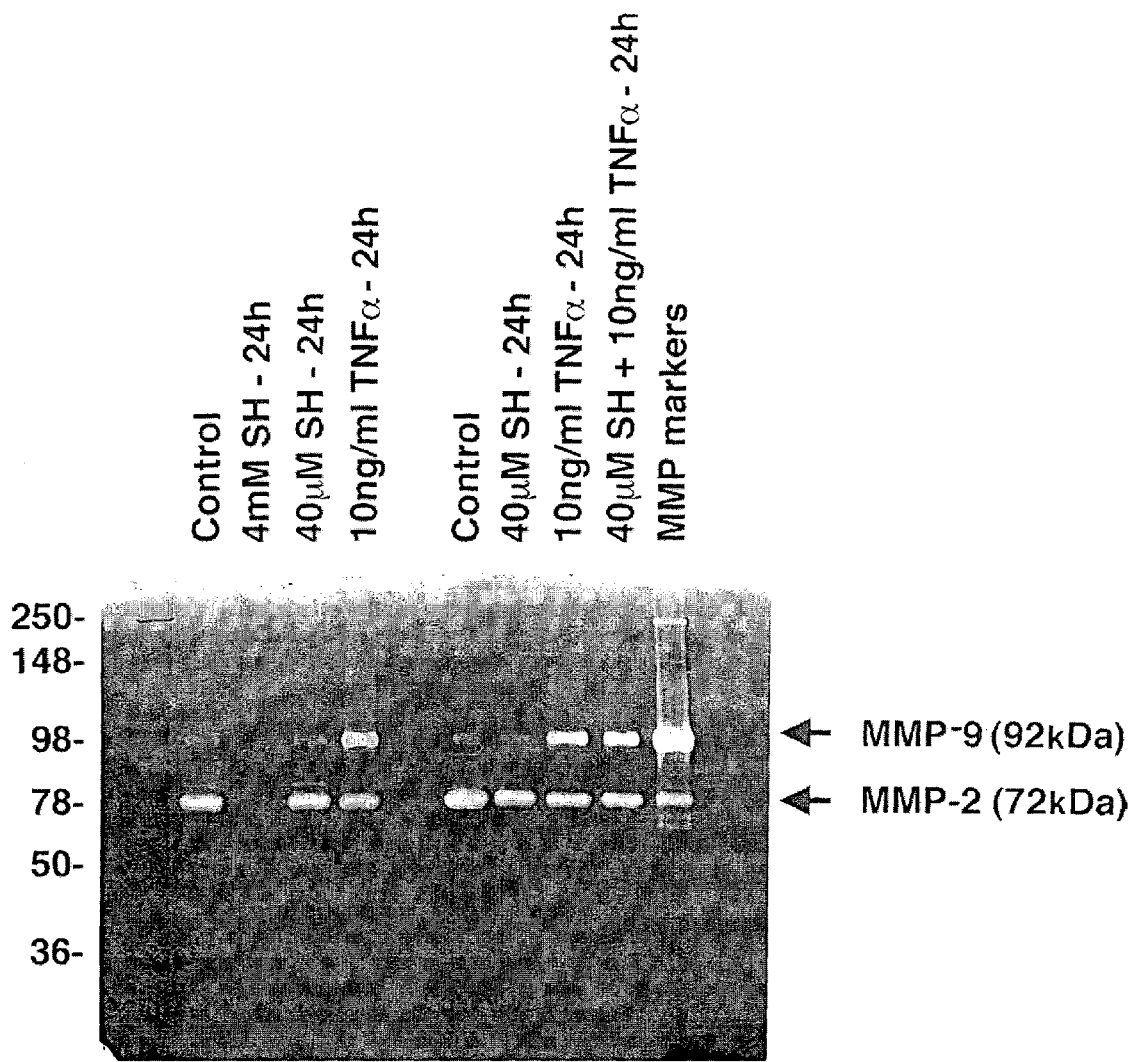
FIG. 3. Effect of Amifostine on MMP Activity. The ability of WR1065, the active thiol of amifostine, to affect the activities of matrix metalloproteinase-2 (MMP-2) and -9 (MMP-9) secreted by human glioma cells and analyzed by gelatin zymography is presented. Following a 24 hr exposure to a 40 micromolar of WR1065 (i.e., SH), MMP-2 activity was reduced to 55% of control levels. A 4 mM concentration of WR1065 completely inhibited MMP-2 and MMP-9 activities. Tumor Necrosis Factor alpha (TNFα) was used as a positive control at a concentration of 10 nanograms/ml. WR1065 (SH) at a dose of 40 micromolar reduced MMP-9 activity by 5% while TNFα enhanced its activity by 85%.
Figure 4:
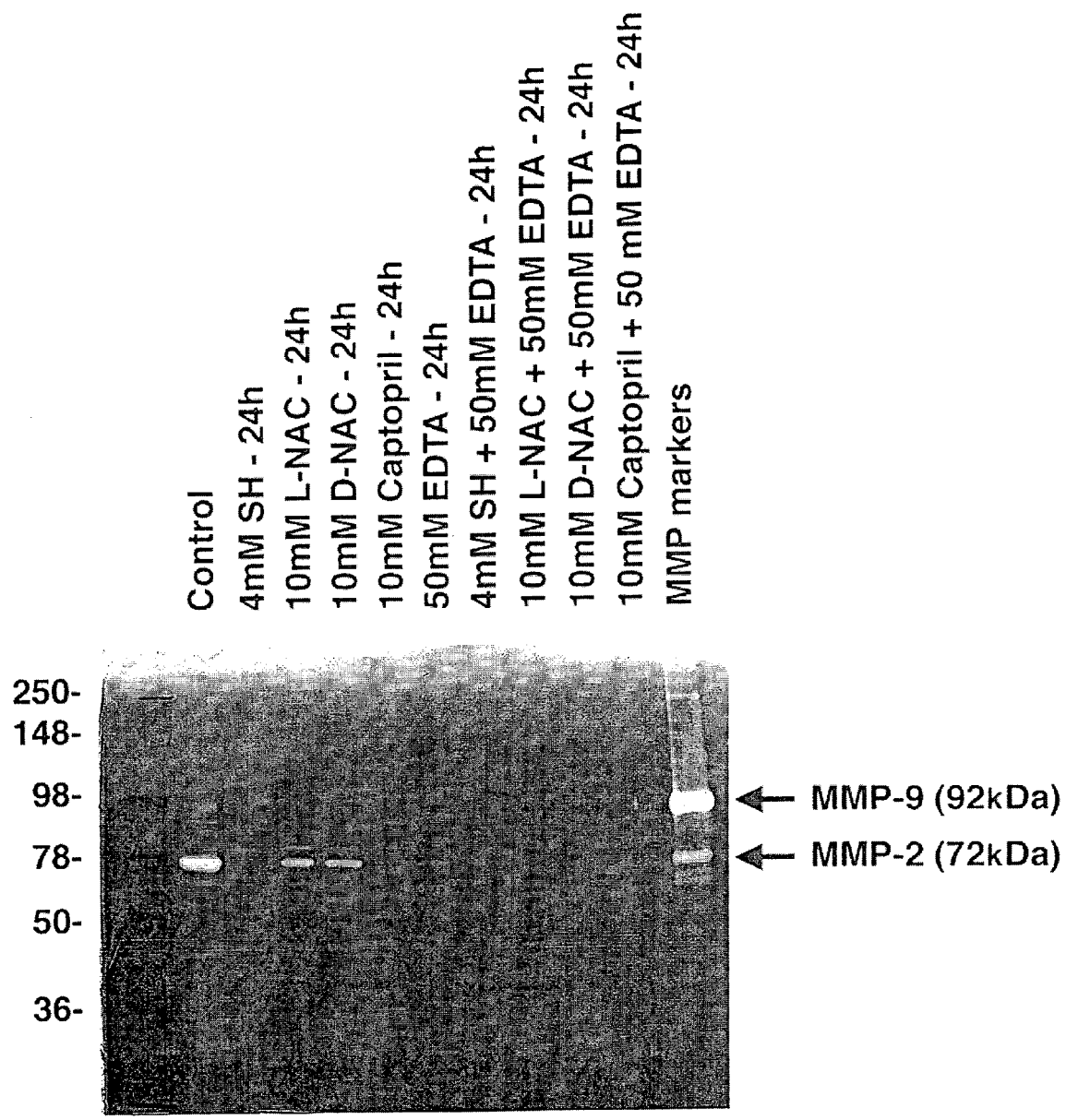
FIG. 4. Comparative Effects on MMP-2 and MMP-9. The relative abilities of mM amounts of WR1065 (SH), N-acetyl-cysteine L form (L-NAC), D form (D-NAC), Captopril, and the chelating agent EDTA (a positive control) on affecting the enzymatic activities of MMP-2 and MMP-9 secreted by human glioma tumor cells following a 24 hr exposure time are contrasted.
Figure 5A:
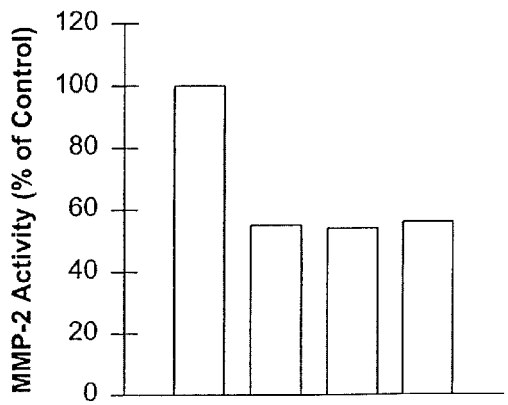
FIG. 5. Quantitative Evaluation. The quantitative evaluation of the gels (see FIGS. 4 and 5) used in the zymography assay by densimetric scanning of gels is presented for comparison.
Figure 5A:
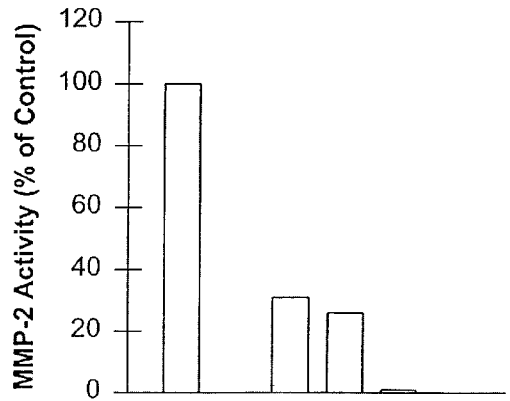
Figure 5B:
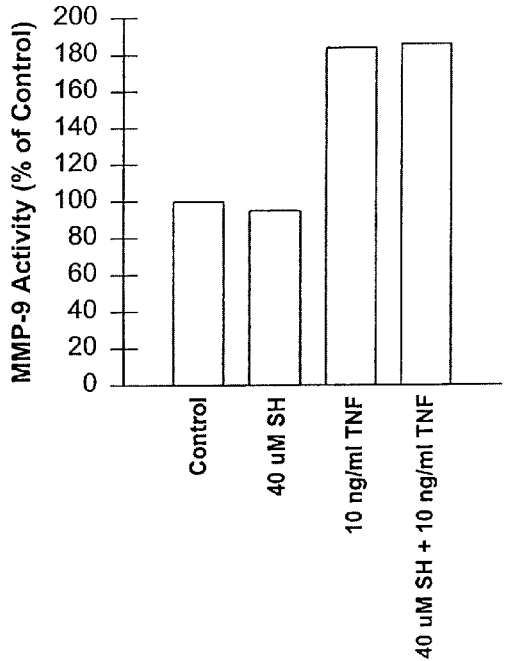
Figure 5B:
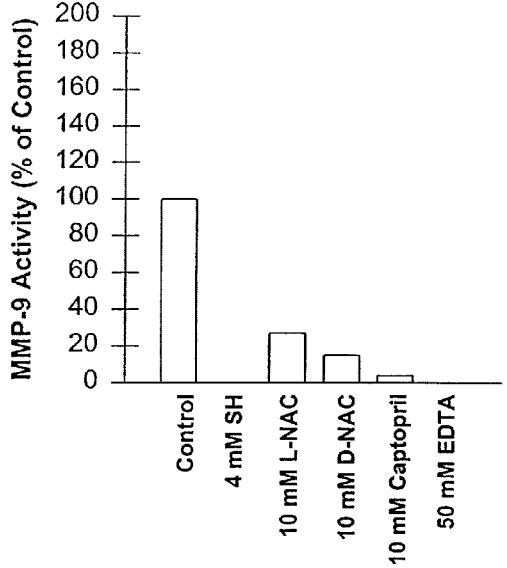

More specifically, the ability of WR-1065 to affect the activities of matrix metalloproteinase-2 (MMP-2) and-9 (MMP-9) in a human glioma cell line is demonstrated in FIG. 3. The effects of L-NAC, D-NAC and captopril are also presented in FIG. 4, and the results of the densimetric scanning of the gels are presented in FIG. 5. Briefly, following a 24 h exposure to a 40 $\mu$M concentration of WR-1065 (SH), MMP-2 activity was reduced to 55% of control levels. TNFα exposure, used as a positive control, at 10 ng/ml was equally effective. The combination of the two agents did not enhance the inhibitory effect (see FIG. 6). For MMP-9, 40 $\mu$M SH reduced activity by only 5%, but in contrast, TNFα enhanced it by about 85%. When concentrations of 4 mM WR-1065 (SH), and 10 mM of L-NAC, D-NAC, or captopril were evaluated, SH and captopril completely inhibited both MMP-2 and MMP-9 activities as did the addition of 50 mM of the metal chelating agent EDTA. NAC at a concentration of 10 mM, regardless of the isomer used, reduced MMP-2 activity by about 69% and MMP-9 by about 75% (see FIGS. 4 and 5). These inhibitory effects of thiols on MMP-2 and MMP-9 may be reversed through the addition of zinc as described elsewhere (Volpert et al., 1996).

As described in Experiments 1 and 2 (see below) exposure of tumor cells to WR-1065 along with other thiols inhibits the enzyme activity of the MMP-2 and does not stimulate MMP-9. A discussion of these enzymes is included in the data set. The ability to inhibit the activity of these tumor-secreted enzymes results in a reduced ability of tumor cells to invade normal tissues and start growth as metastasis.

1. Experiment 1
a. Materials and Methods

U251 Glioma Cells were grown to confluence in 6-well plates. Medium was removed, the cells washed twice with 37° C. PBS, and serum-free medium added. The cells were treated as follows:

Control—24 h, 48 h 72 h
40 $\mu$M SH—24 h, 48 h 72 h (continuous exposure)
10 ng/ml TNFα—24 h, 48 h, 72 h (continuous exposure).

Medium was isolated at the indicated times, centrifuged at 1000 rpm for 5 min to remove debris, and stored at −80° C. until use. Protein was quantitated using the Bradford method. 252 ng of protein was loaded on 10% zymogram (gelatin) gels (Novex, San Diego, Calif.) and electrophoresed at 125 volts for 90 min in Tris-Glycine SDS buffer. After running, the gels were incubated in zymogram renaturing buffer (100 ml) for 30 min at room temperature with gentle agitation. The buffer was removed and fresh zymogram developing buffer (100 ml) added and the gels incubated at 37° C. overnight with gentle agitation. The following day the gels were stained with 0.5% coomassie blue R-250 for 30 min, and destained. Areas of protease activity show up as clear bands. This assay will detect MMP-2 and MMP-9.

b. Results

At 45 h, 40 $\mu$M SH reduced MMP-2 secretion by 45% relative to the control. TNF$\alpha$ reduced MMP-2 by 46%, and the combination reduced MMP-2 by 44%. The ability of 40 $\mu$M SH to reduce MMP-2 secretion was lost at 48 h and 72 h. TNF$\alpha$, however, was still able to suppress MMP-2 secretion at these times. For MMP-9, 40 $\mu$M SH reduced activity by 5% at 24 h, whereas TNF$\alpha$ increased activity by 84%, and for the combination an 86% increase was observed. Again, the ability of 40 $\mu$M SH to affect MMP-9 activity was lost at 48 h and 72 h, while TNF$\alpha$ continued to cause enhanced activity.

2. Experiment 2 a. Materials and Methods

Same protocol as above. Treatment conditions were as follows:

Control—24 h
4 mM SH—24 h (continuous exposure)
10 mM L-NAC—24 h (continuous exposure)
10 mM L-NAC—24 h (continuous exposure)
10 mM Captopril—24 h (continuous exposure)
50 mM EDTA—24 h (chelator)
4 mM SH+50 mM EDTA—24 h
10 mM L-NAC+50 mM EDTA—24 h
10 mM D-NAC+50 mM EDTA—24 h
10 mM Captopril+50 mM EDTA—24 h
40 $\mu$M SH—24 h
10 ng/ml TNF$\alpha$—24 h b. Results 4 mM SH (WR1065) completely inhibited MMP-2 and MMP-9 secretion. L-NAC and D-NAC reduced MMP-2 by 69% and 74% respectively, and MMP-9 by 73% and 85% respectively. Captopril reduced MMP-2 by 99% and MMP-9 by 96%. 50 mM EDTA, which is a metal chelator, completely blocked MMP-2 and MMP-9 secretion, and no activity was seen in the drug+EDTA combinations.

Increase in MnSOD Gene Expression

Figure 6:
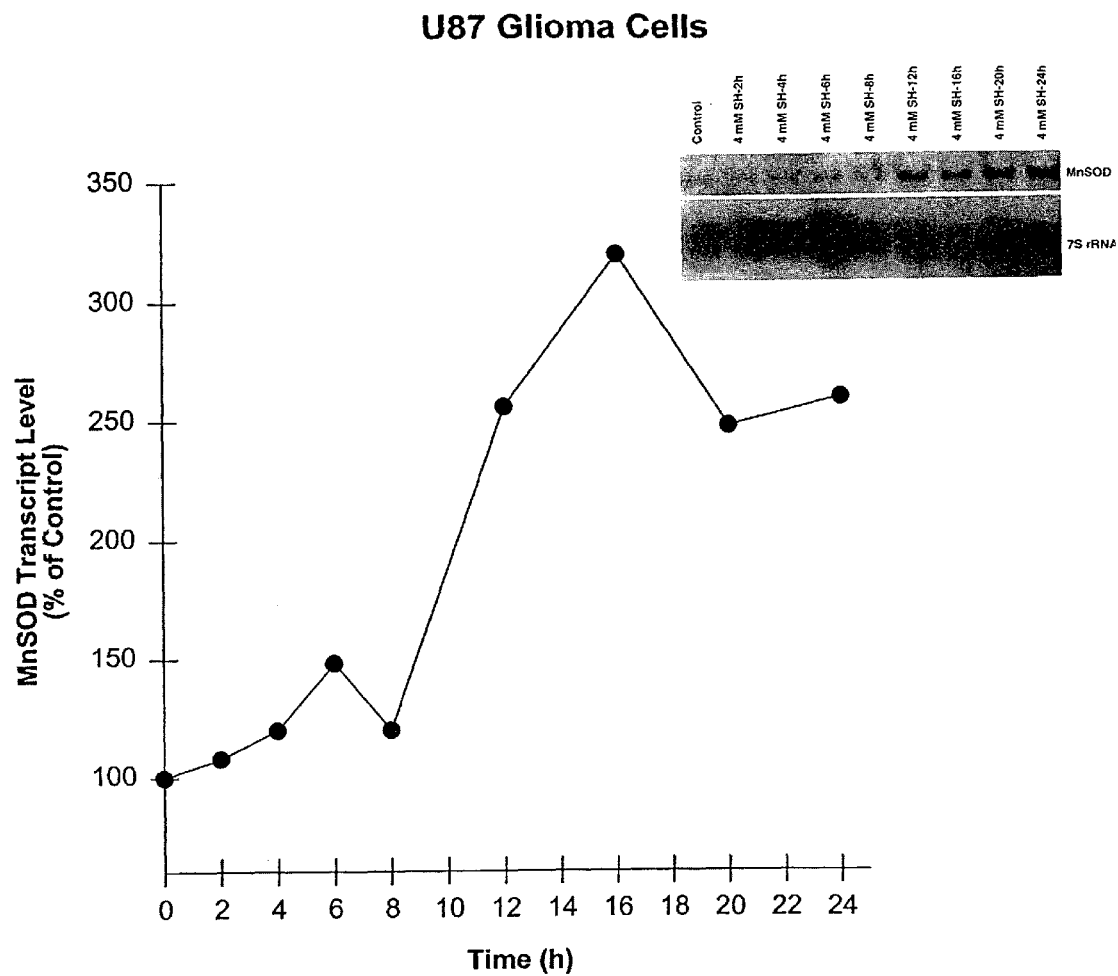
FIG. 6. Effect of Amifostine on MnSOD Expression. Kinetics of manganese superoxide dismutase (MnSOD) gene expression induced in human glioma tumor cells as a function of time by WR1065, the active form of amifostine, are presented for comparison. Also included in the upper right hand corner is a representative Northern blot used to quantitate gene expression. Gene expression was induced over 3-fold as compared to untreated controls.

As previously discussed, manganese superoxide dismutase (MnSOD) has been identified as important anti-oxidant gene whose expression reduces the malignant/metastatic phenotype of cancer cells (Safford et al., 1995). Tumor cells are relatively lower in MnSOD than are normal cells. Increasing MnSOD in tumor cells causes them to loose their ability to be metastatic. As described in FIG. 6, exposure of tumor cells to WR-1065 leads to enhanced gene expression of MnSOD. MnSOD gene expression in human glioma U87 cells was enhanced 2.5 fold after 12 h, and remained at that elevated level for an additional 12 h (FIG. 6). The peak level of MnSOD expression was almost twice that observed in normal human endothelial cells exposed to WR-1065. Enhanced expression of MnSOD in tumor cells will result in a less malignant phenotype as demonstrated by a reduction in the ability to form metastases (Liu et al., 1997; Li et al., 1998).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Documents
U.S. Pat. No. 5,567,686
U.S. Pat. No. 5,488,042
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 5,869,338
U.S. Pat. No. 5,891,856

Ahmad and Hart, "Mechanisms of metastasis," *Crit. Rev. Oncol. Hematol.*, 26(3):163–173, 1997.

Alberg, Visvanathan, Helzlsouer, "Epidemiology, prevention, and early detection of breast cancer," *Curr. Opin. Oncol.*, 10(6):492–497, 1998.

Albini, D'Agostini, Giunciuglio, Paglieri, Balansky, DeFlora, "Inhibition of invasion, gelatinase activity, tumor take and metastasis of malignant cells by N-acetylcysteine," *Int. J. Cancer*, 61:121–129, 1995.

Antras-Ferry, Maheo, Chevanne, Dubos, Morel, Guillouzo, Cillaed, Cillard, "Oltipraz stimulates the transcription of the manganese superoxide dismutase gene in rat hepatocytes," *Carcinogenesis*, 18(11):2113–2117, 1997.

Apffel, Walker, Issarescu, "Tumor rejection in experimental animals treated with radioprotective thiols," *Cancer Res.*, 35:429–437, 1975.

Austin-Ward, Villaseca, "Gene therapy and its applications," *Rev. Med. Chil.*, 126(7):838–45, 1998.

Baichwal and Sugden, In: *Gene Transfer*, Kucherlapati R, ed., New York, Plenum Press, pp. 117–148, 1986.

Banner, Koch, Capin, Hopf, Chang, Tong, "Experimental chelatio therapy in chromium, lead, and boron intoxication with N-acetylcysteine and other compounds," *Toxicol. Appl. Pharmacol.*, 83:142–147, 1986.

Benson III, "Oltipraz: A laboratory and clinical review," *J. Cell. Biochem.*, 17(F):278–291, 1993.

Bhatia, Robinson, Oberlin, Greenberg, Bunin, Fossati-Bellani, Meadows, "Breast cancer and other second neoplasms after childhood Hodgkin's disease," *New England J. Med.*, 334(12):745–751, 1996.

Brown, Thompson, Milas, "Effects of size and growth time of a murine sarcoma on its metastatic spread," *Clin. Exp. Metastasis*, 10(1):77–86, 1992.

Brown P D. "Matrix metalloproteinase inhibitors in the treatment of cancer." *Med. Oncol.* 14:1–10, 1997.

Brumas, Hacht, Filella, Berthon, "Can N-acetyl-L-cysteine affect zinc metabolism when used as a paracetamol antidote?" *Agents Actions*, 36:278–288, 1992.

Bukowski, Rayman, Uzzo, Bloom, Sandstrom, Peereboom, Olencki, Budd, McLain, Elson, Novick, Finke, "Signal transduction abnormalities in T lymphocytes from patients with advanced renal carcinoma: clinical relevance and effects of cytokine therapy," *Clin. Cancer Res.*, 4(10):2337–47, 1998.

Carnes and Grdina, "In vivo protection by the aminothiol WR-2721 against neutron-induced carcinogenesis," *Int. J. Radiat. Biol.*, 61:567–576, 1992.

Chen and Okayama, *Mol. Cell Biol.*, 7:2745–2752, 1987.

Christodoulides, Brooks, Rattue, Heckels, "Immunization with recombinant class 1 outer-membrance protein from *Neisseria meningitidis*: influence of liposomes and adjuvants on antibody avidity, recognition of native protein and the induction of a bactericidal immune response against meningococci," *Microbiology*, 144(Pt 11):3027–37, 1998.

Clement, Musso, Lietard, Theret, "Homeostatic control of angiogenesis: a newly identified functino of the liver?" *Hepatology*, 29(3):621–623, 1999.

Coupar et al., *Gene*, 68:1–10, 1988.

Das, Lewis-Molock, White, "Activation of NF-κB and elevation of MnSOD gene expression by thiol reducing agents in lung adenocarcinoma (A549) cells," *Am. J. Physiol.*, 269:L588–L602, 1995.

Davidson, Musk, Wood, Morey, Ilton, Yu, Drury, Shilkin, Robinson, "Intralesional cytokine therapy in cancer: a pilot study of GM-CSF infusion in mesothelioma," *J. Immunother.*, 21(5):389–98, 1998.

De Flora, Bennicelli, Camoirano, Serra, Romano, Rossi, Morelli, De Flora, "In vivo effects of N-acetylcysteine on gluthathione metabolism and on the biotransformation of carcinogenic and/or mutagenic compounds," *Carcinogenesis*, 6(12):1735–1745, 1985.

De Flora, Cesarone, Balansky, Albini, D'Agostini, Bennicelli, Bagnasco, Camoirano, Scatolini, Rovida, "Chemopreventive properties and mechanisms of N-acetylcysteine. The experimental background," *J. Cell Biochem. Suppl.*, 22:33–41, 1995.

DeFlora, D'Agostini, Masiello, Giunciuglio, Albini, "Synergism between N-acetylcysteine and doxorubicin in the prevention of tumorigenicity and metastasis in murine models," *Int. J. Cancer*, 67(6):842–848, 1996.

Devi and Prasanna, "Radioprotective effect of combinations of WR-2721 and mercaptopropionyglycine on mouse bone marrow chromosomes," *Radiat. Res.*, 124:165–170, 1990.

Deyi and Prasana, "Radioprotective effect of combinations of WR-2721 and mercaptopropionylglycine on mouse bone marrow chromosomes," *Radiat. Res.*, 124:165–170, 1990.

Dijkwel and Wenink, "Structural integrity of the nuclear matrix: differential effects of thiol agents and metal chelators," *T. Cell Sci.*, 84:53–67, 1986.

Dorr, "Radioprotectants: pharmacology and clinical applications of amifostine," *Semin. Radiat. Oncol.*, 8(4 Supp 1):10–13, 1998.

Duivenvoorden, Hirte, Singh, "use of tetracycline as an inhibitor of matrix metalloproteinase activity secreted by human bone-mestastasizing cancer cells," *Invasion Metastasis*, 17:312–322, 1997.

Falcone, Khan, Layne, Fernandes, "Macrophage formation of angiostatin during inflamation," *J. Biol. Chem.*, 273(47):31480–31485, 1998.

Fechheimer et al., *Proc. Natl. Acad. Sci. USA*, 84:8463–8467, 1987.

Fink, Carlson, Boehm, McTaggart, Qiao, Doughty, Granu, Melton, Goldberg, "Design and synthesis of thiol containing inhibitors of matrix metallaproteinases," *Bioorg. Med. Chem. Lett.*, 9:195–200, 1999.

Foster-Nora and Siden, "Amifostine for protection from antineoplastic drug toxicity," *Am. J. Health Syst. Pharm.*, 54(7):787–800, 1997.

Fraley et al., *Proc. Natl. Acad. Sci. USA*, 76:3348–3352, 1979.

Freskos, Mischke, DeCrescenzo, Heintz, Getman, Howard, Kishore, McDonald, Munie, Rnagwals, Swearingen, Voliva, Welsch, "Disvoery of a novel series of selective MMP inhibitors: identification of the γ-fulfone-thiols," *Bioorg. Med. Chem, Lett.*, 9:943–948, 1999.

Gately, Twardowski, Stack, Cundiff, Grella, Castellano, Enghild, Kwaan, Lee, Kramer, Volpert, Bouck, Soff, "The mechanism of cancer-mediated converstion of plasminogen to the angiogenesis inhibitor angiostatin," *Proc. Natl. Acad Aci. USA*, 94:10868–10872, 1997.

Gately, Twardowski, Stack, Patrick, Boggio, Cundiff, Schnaper, Madison, Volpert, Bouck, Enghild, Kwaan, Soff, "Human prostate carcinoma cells express enzymatic activity that converts human plasminogen to the angiogenesis inhibitor, angiostatin," *Cancer Res.*, 56:4887–4890, 1996.

Giambarresi and Jacobs, "Radioprotectants in Military Radiobiology," eds. J. J. Conklin and R. I. Walker, Academic Press Inc., Orlando, Fla., pp. 265–301, 1987.

Gilbert, "Redox control of enzyme activities by thiol/disulfide exchange," *In: Methods in Enzymology*, Academic Press, New York, 107:330–351, 1984.

Gopal, *Mol. Cell Biol.*, 5:1188–1190, 1985.

Graham and Van Der Eb, *Virology*, 52:456–467, 1973.

Grdina, Hittleman, White, Meistrich, "The formation of lung colonies. An analysis based on cellular parameters of density, size, and DNA content," *Brit. J. Cancer*, 36:659–669, 1977.

Grdina, Hunter, Kataoka, Murley, Milas, "Chemopreventive doses of Amifostine confer no cytoprotection to tumor nodules growing in the lungs of mice treated with cyclophosphamide," *Sem. Oncol.*, 26 Supp. 2: 22–27, 1999.

Grdina, Kataoka, Basic, Perrin, "The radioprotector WR-2721 reduces neutron induced mutations at the hypoxanthine-guanine phosphoribosyl transferase locus in mouse splenocytes when administered prior to or following irradiation," *Carcinogenesis*, 61(5):811–814, 1992.

Grdina, Milas, Mason, Withers, "Separation of cells from a fibrosarcoma in renografin gradients," *J. Nat'l. Cancer Inst.*, 52:253–257, 1974.

Grdina, Peters, Jones, Chan, "Separation of cells from a murine fibrosarcoma on the basis of size. I. Relationship between cell size and age as modified by growth in vivo and in vitro," *J. Nat'l Cancer Inst.*, 61:209–214, 1978.

Grdina, Peters, Jones, Chan, "Separation of cells rom a murine fibrosarcoma on the basis of size. II. Differential effects of cell size and age on lung retention and colony formation in normal and pre-conditioned mice," *J. Nat'l. Cancer Inst.*, 61:215–220, 1978.

Grdina, Shigematsu, Dale, Newton, Aguilera, Fahey, "Thiol and disulfide metabolites of the radiation protector and potential chemopreventive agent WR-2721 are linked to both its anti-cytotoxic and anti-mutagenic mechanisms of action," *Carcinogenesis*, 16:767–774, 1995.

Hanibuchi, Yano, Nishioka, Yanagawa, Kawano, Sone, "Therapeutic efficacy of mouse-human chimeric antiganglioside GM2 monoclonal antibody against multiple organ micrometastases of human lung cancer in NK cell-depleted SCID mice," *Int. J. Cancer*, 78(4):480–5, 1998.

Hayes, Bouchier, Beckett, "Glutathione-S-transferase in humans in health and disease," *Gut*, 32:813–818, 1991.

Hellstrand, Hermodsson, Naredi, Mellqvist, Brune, "Histamine and cytokine therapy," *Acta. Oncol.*, 37(4):347–53, 1998.

Hirschel-Scholz et al., "Interference of WR-2721 with magnesium metabolism: mechanism of action," *Miner Electrolyte Metab.*, 14(2–3):114–20, 1988.

Hoffman, Starkey, Coad, "Would fluid from venous leg ulcers degrades plasminogen and reduces plasmin generation by keratinocytes," *J. Invest Dermatol.*, 111:1140–1144, 1998.

Hong and Sporn, "Recent advances in chemoprevention of cancer," *Science*, 278:1073–1077, 1997.

Hui and Hashimoto, "Pathways for potentiation of immunogenicity during adjuvant-assisted immunizations with *Plasmodium falciparum* major merozoite surface protein 1," *Infect. Immun.*, 66(11):5329–36, 1998.

Issels, Nagele, Eckert, Wilmanns, "Promotion of cystine uptake and its utilization for gluthathione synthesis induced by cysteamine and N-acetylcysteine," *Biochem Pharmacol.*, 37:881–888, 1988.

Johnson, "Second lung cancers in patients after treatment for an initial lung cancer," *J. Nat'l. Cancer Inst.*, 90(18):1335–1345, 1998.

Kahari and Saarialho-Kere, "Matrix metalloproteinases and their inhibitors in tumor growth and invasion," *Ann. Med.*, 31:34–45, 1999.

Karp and Smith, "The molecular pathogenesis of treatment-induced (secondary) leukemias: foundations for treatment and prevention," *Semin. Oncol.*, 8(4 Suppl 1):10–13, 1997.

Kataoka, Basic, Perrin, Grdina, "Anti-mutagenic effects of the radioprotector WR-2721 against fission spectrum neutrons and $^{60}$Co γ-rays in mice," *Int. J. Radiat. Biol.*, 61:387–392, 1992.

Kataoka, Perrin, Grdina, "Induction of hprt mutations in mice following exposure to fission spectrum neutrons or $^{60}$Co γ rays," *Radiat. Res.*, 136:289–292, 1993.

Kataoka, Perrin, Hunter, Milas, Grdina, "Anti-mutagenic effects of amifostine: clinical implications," *Semin. Oncol.*, 23(8):53–57, 1996.

Kelloff, Boone, Crowell, Steele, Lubet, Sigman, "Perspectives and progress," *Cancer Epidemoil. Biomark. Prev.*, 3:85–98, 1994.

Kelloff, Crowell, Boone, Steele, Lubet, Greenwald, Alberts, Covey, Doody, Knapp et al., "Strategy and planning for chemopreventive drug development: clinical development plans," *J. Cell. Biochem. Suppl.*, 20:55–62, 1994.

Kensler and Helzlsouer, "Oltipraz: Clinical opportunities for cancer chemoprevention," *J. Cell. Biochem.*, 22:101–107, 1995.

Kim and Gates, "Evidence for thiol-dependent production of oxygen radicals by 4-methyl-5-pyrazinyl-3H-1,2-dithiole-3-thione (Oltipraz) and the 3H-1,2-dithiole-3-thione: Possible relevance to the anticarcinogenic properties of 1,2-dithiole-3-thiones," *Chem. Res. Toxicol.*, 10(3):296–301, 1997.

Kleiner D E, and Stetler-Stevenson W G. "Structural biochemistry and activation of matrix metalloproteinases." *Curr. Opinion Cell Biol.* 5:891–897, 1993.

Kleiner and Stetler-Stevenson, "Matrix metalloproteinases and metastasis," *Cancer Chemother. Pharmacol.*, 43:S42–S51, 1999.

Langeland, Morris, McKinley-McKee, "Metal binding properties of thiols; complexes with horse liver alcohol dehydrogenase," *Comp, Biochem. Physiol.*, 123(Part B):155–162, 1999.

Lannutti, Gately, Quevedo, Soff, Paller, "Human angiostatin inhibits murine hamangioendothelioma tumor growth in vivo," *Cancer Res.*, 57:5277–5280, 1997.

Leverger, Carrere, Caudry, Garabedian, Anosolborlo, Vergnes, "Second thyroid neoplasms after prophylactic cranial irradiation for acute lymphoblastic leukemia," *Am. J. Hematol.*, 59(1):91–94, 1998.

Li, Oberley, Oberley, Zhong, "Overexpression of Manganese Superoxide Dismutase in DU145 human prostate carcinoma cells has multiple effects on cell phenotype," *The Prostate*, 35:221–233, 1998.

Liu, Oberley, Oberley, "Transfection and expression of MnSOD cDNA decreases tumor malignancy of human oral squamous carcinoma SCC-25 cells," *Human Gene Ther.*, 8:585–595, 1997.

Lovejoy, Cleasby, Hassell, Longley, Luther, Weigl, McGeehan, McElroy, Drewry, Lambert, and Jordan. Structure of the catalytic domain of fibroblast collagenase complexed with an inhibitor. *Science* 263:375–1994.

Llobert and Domingo, "Comparative effects of repeated parenteral administration of several chelators on the distribution and excretion of cobalt," *Res. Comm. Chem. Path, Pharmacol.*, 60(2):255–233, 1988.

McChesney, Gillette, Dewhirst, Withrow, "Influence of WR-2721 on radiation response of canine soft tissue sarcomas" *Int. J. Radiat. Oncol. Biol. Phys.*, 12:1957–1963, 1986.

McDonnell, De Guzman, Rice, Turpin, Summers, "Zinc ejection as a new rationale for the use of a cystamine and related disulfide-containing antiviral agents in the treatment of AIDS," *J. Med. Chem.*, 40(13):1969–76, 1997.

Meyskens, "Chemoprevention of cancer in humans 1990: Where do we go from here?" *In: Chemoimmuno Prevention of Cancer*, 1st Conf., Vienna, Austria, Pastorino and Hong (eds.), Georg Thieme Verlag Thieme Medical Publishers, Inc., NY, N.Y., pp. 245–252, 1991.

Milas, Hunter Stephens, Peters, "Inhibition of radiation carcinogenesis by S-2-(3-aminopropylamino) ethylphosphorothioic acid," *Cancer Res.*, 44:5567–5569, 1984.

Milas, Hunter, Ito, Peters, "Effect of tumor type, size, and endpoint on tumor radioprotection by WR-2721," *Int. J. Radiat. Oncol. Biol. Phys.*, 10:41–48, 1984.

Morse and Stoner, "Cancer chemoprevention: principles and prospects," *Carcinogenesis*, 14(9):1737–1746, 1993.

Newton, Aguilera, Ward, Fahey, "Binding of radioprotective thiols and disulfides in Chinese hamester V79 cell nuclei," *Radiat. Res.*, 146:298–305, 1996.

Nicolau and Sene, *Biochim. Biophys. Acta*, 721:185–190, 1982.

Nicolson, Custead, Dulski, Milas, "Effects of gamma irradiation on cultured rat and mouse microvessel endothelial cells: metastatic tumor adhesion, subendothelial matrix degradation, and secretion of tumor cell growth factors," *Clin. Exp. Metastasis*, 9(5):457–468, 1991.

Package insert for Ethyol®, ALZA Pharmaceuticals, a Division of ALZA Corp., and US Bioscience, Inc., 1997.

Penhaligon, "Radioprotection of mouse skin vasculature and the RIF-1 fibrosarcoma by WR-2721," *Int. J. Radiat. Oncol. Biol. Phys.*, 10:1541–1544, 1984.

Pietras, Pegram, Finn, Maneval, Slamon, "Remission of human breast cancer xenografts on therapy with humanized monoclonal antibody to HER-2 receptor and DNA-reactive drugs," *Oncogene*, 17(17):2235–49, 1998.

Pinkus, Weiner, Daniel, "Role of oxidants and antioxidants in the induction of AP-1, NFκB, and glutathione S-transferase gene expression," *J. Biol. Chem.*, 271(23):13422–13429, 1996.

Polla, Donati, Kondo, Tochon-Danguy, Bonjour, "Protection from cellular oxidative injury and calcium intrusion by n-(2-mercaptoethyl)-1,3-propanediamine, WR 1065," *Biochem. Pharmacol.*, 40(7):1469–1475, 1980.

Potter et al., *Proc. Nat. Acad. Sci. USA*, 81:7161–7165, 1984.

Prontera, Mariani, Rossi, Poggi, Rotilio, "Inhibition of gelatinase A (MMP-2) by batimastat and captopril reduces tumor growth and lunc metastases in mice bearing lewis lung carcinoma," *Int. J. Cancer*, 81:761–766, 1999.

Qin, Tao, Dergay, Moy, Fawell, Davis, Wilson, Barsoum, "Interferon-beta gene therapy inhibits tumor formation and causes regression of established tumors in immune-deficient mice," *Proc. Nat'l Acad. Sci. USA*, 95(24): 1411–6, 1998.

Rasey, Krohn, Menard, Spence, "Comparative biodistribution and radioprotection studies with three radioprotective drugs in mouse tumors," *Int. J. Radiat. Oncol. Biol. Phys.*, 12:1487–1490, 1986.

Ridgeway, In: *Vectors: A survey of molecular cloning vectors and their uses*, Rodriguez R L, Denhardt D T, ed., Stoneham:Butterworth, pp. 467–492, 1988.

Rippe et al., *Mol. Cell Biol.*, 10:689–695, 1990.

Sack, Beaton and Sathe, "Diurnal variations in angiostatin in human tear fluid: a possible role in prevention of corneal neovascularization," *Curr. Eye Res.*, 18(3):186–193, 1999.

Safford, Oberley, Urano, St. Clair, "Suppression of fibrosarcoma metastasis by elevated expression of Manganese Superoxide Dismutase," *Cancer Res.*, 54:4261–4265, 1994.

Schimming, Mason, Hunter, Weil, Kishi, Milas, "Lack of correlation between mitotic arrest or apoptosis and anti-tumor effect of docetaxel," *Cancer Chemother. Pharmacol.*, 43(2):165–172, 1999.

Sen, "Redox signaling and the emerging therapeutic potential of thiol antioxidants," *Biochem. Pharmacol.*, 55:1747, 1758, 1998.

Shapiro S D, and Senior R M. "Matrix metalloproteinases: Matrix degradation and more." *Am. J. Respir. Cell Molec. Biol.* 20:1100–1102, 1999.

Spencer and Goa, "Amifostine: "A review of its pharmacodynamic and pharmacokinetic properties, and therapeutic potential as a radioprotector and cytotoxic chemoprotector," *Drugs*, 50(6):1001–1031, 1995.

Springman E B, Angleton E L, Birkedal-Hansen H, and Van Wart H E. Multiple modes of activation of latent human fibroblast collagenase: evidence for the role of a Cys73 active-site zinc complex in latency and a cysteine switch mechanism for activation. *Proc. Natl. Acad. Sci. USA* 897:364–1990.

Stathakis, Fitzgerald, Matthias, Chesterman, Hogg, "Generation of angiostatin by reduction and proteolysis of plasmin," *J. Biol. Chem.*, 272(33):20641–20645, 1997.

Stathakis, Lay, Fitzgerlad, Schlieker, Matthias, Hogg, "Angiostatin formation involves disulifide bond reduction and proteolysis in kringle 5 of plasmin," *J. Biol. Chem.*, 274(13):8910–8916, 1999.

Stetler-Stevenson W G. Matrix metalloproteinases in angiogenesis: a moving target for therapeutic intervention. *J. Clin. Invest.* 103:1237–1241, 1999.

Stewart, Rojas, Denekamp, "Radioprotection of two mouse tumors by WR-2721 in single and fractionated treatments," *Int. J. Radiat. Oncol. Biol. Phys.*, 9:507–513, 1983.

Sugimura, Umezawa, Matsushima, Sawamura, Seino, Yahagi, Nagao, "Mutagenecity of cancer drugs-prediction of the risk of a second tumor and use of the mutation test for monitoring improvement of drugs," In: *Advances in Cancer Chemotherapy*, Umezawa et al. (eds.), Japan Sci. Soc. Press, Tokyo University Park Press, Baltimore, Md., pp. 283–296, 1978.

Suzuki, Frapart, Grdina, Meistrich, Withers, "Cell cycle dependency of metastatic lung colony formation," *Cancer Res.*, 37:3690–3693, 1977.

Sweeney, "A survey of compounds from the antiradiation drug development program of the U.S. Army Medical Research and Development Command," Walter Reed Army Institute of Research, Washington, D.C., September 1979.

Tur-Kaspa et al., *Mol. Cell Biol.*, 6:716–718, 1986.

Tuttle, Horan, Koch, Held, Manevich, Biaglow, "Radiation-sensitive tyrosine phosphorylation of cellular proteins: sensitive changes to GSH content induced by pretreatment with N-acetyl-1-cysteine or 1-buthionine-S, R-sulfoximine," *Int. J. Radiat. Oncol. Biol. Phys.*, 42(4):833–838, 1998.

Urano, Kuroda, Reynolds, Oberley, St. Clair, "Expression of manganese superoxide dismutase reduces tumor control radiation dose: gene-radiotherapy," *Cancer Res.*, 55:2490–2493, 1995.

Volpe and Milas, "Metastatic instability of murine tumor metastases: dependence on tumor type," *Clin. Exp. Metastasis*, 6(4):333–346, 1988.

Volpe, Basic, Milas, "Metastatic abilities of murine sarcomas and carcinomas. II. relationship to cell volume and DNA index," *Clin. Exp. Metastasis*, 8(2):193–201, 1990.

Volpe, Hunter, Basic, Milas, "Metastatic properties of murine sarcomas and carcinomas, I. Positive correlation with lung colonization and lack of correlation with s.c. tumor take," *Clin. Exp. Metastasis*, 3(4):281–294, 1985.

Volpert, Ward, Lingen, Chesler, Solt, Johnson, Molteni, Polverini, Bouck, "Captopril inhibits angiogenesis and slows the growth of experimental tumors in rats," *J. Clin. Invest.*, 98(3):671–679, 1996.

Walpole and Myers, In: *Probability and Statistics for Engineers and Scientists*, 2d Ed., Macmillan Publishing Co., Inc., NY, N.Y., pp. 263–265, 1978.

Woloschak, Paunesku, Chang-Liu, Grdina, "Expression of thymidine kinase messenger RNA and a related transcript is modulated by the radioprotector WR-1065," *Cancer Res.*, 55:4788–4792, 1995.

Wu and Wu, *Biochem.*, 27:887–892, 1988.

Wu and Wu, *J. Biol. Chem.*, 262:4429–4432, 1987.

Yang et al., *Proc. Nat'l. Acad. Sci USA*, 87:9568–9572, 1990.

Zetter, "Angiogenesis and tumor metastasis," *Annu. Rev. Med.*, 49:407–424, 1998.

What is claimed is:

1. A method for reducing the number of lung metastases in an animal exhibiting a primary tumor comprising administering to said animal a dose of 50 mg/kg to 100 mg/kg of WR-2721, wherein the number of metastases is reduced in the lung.

2. The method of claim 1, wherein said tumor is a sarcoma or carcinoma.

3. The method claim 1, wherein said WR-2721 is the thiol form.

4. The method claim 1, wherein said WR-2721 is the disulfide form.

5. The method of claim 1, wherein the route of administration of said WR-2721 is intravenous, intraperitoneal, intradermal, intramuscularal, dermal, nasal, buccal, rectal, vaginal, inhalation, or topical.

6. The method of claim 1, wherein said WR-2721 is formulated into solutions, suspensions, tablets, pills, capsules, sustained release formulations, powders, creams, ointments, salves, sprays, pumps, liposomes, suppositories, inhalers, or patches.

7. The method of claim 1, further comprising monitoring the ability of the dose of WR-2721 to reduce metastases in the animal.

8. The method of claim 7, wherein the monitoring comprises measuring the level of angiostatin stimulation.

9. The method of claim 7, wherein the monitoring comprises measuring the level of activity of a matrix metalloproteinase.

10. The method of claim 9, wherein the matrix metalloproteinase is MMP-2.

11. The method of claim 9, wherein the matrix metalloproteinase is MMP-9.

12. The method of claim 7, wherein the monitoring comprising measuring the stimulation of MnSOD.

13. The method of claim 12, wherein the measuring of MnSOD stimulation comprises measuring the stimulation of MnSOD gene expression.

14. A method for inhibiting lung metastasis in an animal exhibiting a primary tumor comprising administering to said animal a dose of 50 mg/kg to 100 mg/kg of WR-2721, wherein the number of lung metastases is inhibited.

* * * * *